US010758378B2

(12) United States Patent
Steele et al.

(10) Patent No.: US 10,758,378 B2
(45) Date of Patent: Sep. 1, 2020

(54) PROSTHETIC WITH VOICE COIL VALVE

(71) Applicant: FREEDOM INNOVATIONS, LLC, Irvine, CA (US)

(72) Inventors: Wilson Steele, Huntington Beach, CA (US); Michael Palmer, Ladera Ranch, CA (US); Stephen Prince, Irvine, CA (US); Charlie Bisbee, Irvine, CA (US); Henry Hsu, Aliso Viejo, CA (US)

(73) Assignee: Freedom Innovations, LLC, Irvine, CA (US)

( * ) Notice: Subject to any disclaimer, the term of this patent is extended or adjusted under 35 U.S.C. 154(b) by 0 days.

(21) Appl. No.: 15/817,114

(22) Filed: Nov. 17, 2017

(65) Prior Publication Data

US 2018/0289513 A1    Oct. 11, 2018

Related U.S. Application Data

(63) Continuation of application No. 14/707,957, filed on May 8, 2015, now abandoned, which is a continuation
(Continued)

(51) Int. Cl.
*A61F 2/68* (2006.01)
*A61F 2/64* (2006.01)
(Continued)

(52) U.S. Cl.
CPC .................. *A61F 2/68* (2013.01); *A61F 2/64* (2013.01); *A61F 2002/5003* (2013.01);
(Continued)

(58) Field of Classification Search
CPC ............ A61F 2002/748; A61F 2002/74; A61F 2002/702; A61F 2002/768;
(Continued)

(56) References Cited

U.S. PATENT DOCUMENTS 2,465,585 A    3/1947  Ganoe et al.
2,470,480 A    5/1949  Fogg
(Continued)

FOREIGN PATENT DOCUMENTS

DE    811714 C      8/1951
DE    4410730 C1    6/1995
(Continued)

OTHER PUBLICATIONS

Bloch, Heinz, (Dec. 18, 2005). "Pump Repair and Restoration Guidelines", Chemical Processing Industry News, 8 pages.
(Continued)

*Primary Examiner* — Christie L Bahena
(74) *Attorney, Agent, or Firm* — Dorsey & Whitney LLP

(57) ABSTRACT

A prosthetic includes a pair of prosthetic members movably coupled together to allow movement of the pair of prosthetic members with respect to one another. A hydraulic actuator or damper including hydraulic fluid in a hydraulic chamber is coupled to one of the pair of prosthetic members. A hydraulic piston is movably disposed in the hydraulic chamber and coupled to another of the pair of prosthetic members. A hydraulic flow channel is fluidly coupled between opposite sides of the chamber to allow hydraulic fluid to move between the opposite sides of the chamber as the hydraulic piston moves therein. A voice coil valve is coupled to the hydraulic flow channel to vary resistance to flow of hydraulic fluid through the flow channel, and thus movement of the piston in the chamber, and thus influencing a rate of movement of the pair of prosthetic members with respect to one another.

14 Claims, 20 Drawing Sheets

Related U.S. Application Data of application No. 13/829,714, filed on Mar. 14, 2013, now Pat. No. 9,028,557.

(51) Int. Cl.
    *A61F 2/74*     (2006.01)
    *A61F 2/76*     (2006.01)
    *A61F 2/50*     (2006.01)

(52) U.S. Cl.
    CPC ........ *A61F 2002/5006* (2013.01); *A61F 2002/5033* (2013.01); *A61F 2002/5035* (2013.01); *A61F 2002/74* (2013.01); *A61F 2002/741* (2013.01); *A61F 2002/744* (2013.01); *A61F 2002/745* (2013.01); *A61F 2002/748* (2013.01); *A61F 2002/7635* (2013.01)

(58) Field of Classification Search
    CPC ........ A61F 2002/7635; A61F 2002/745; A61F 2002/741; A61F 2002/5035; A61F 2002/5033; A61F 2002/5006; A61F 2002/5003; A61F 2002/744; A61F 2/68; A61F 2/64

See application file for complete search history.

(56) References Cited

U.S. PATENT DOCUMENTS

| | | | |
|---|---|---|---|
| 2,843,853 A | | 7/1958 | Mauch |
| 3,053,236 A | | 9/1962 | Self et al. |
| 3,457,956 A | | 7/1969 | Andrews |
| 3,457,959 A | | 7/1969 | Cooper |
| 3,749,128 A | | 7/1973 | Sallberg et al. |
| 3,871,032 A | | 3/1975 | Karas |
| 4,134,424 A | * | 1/1979 | Zeyra ............ F16K 17/19 137/493 |
| 4,838,392 A | | 6/1989 | Miller et al. |
| 5,021,064 A | * | 6/1991 | Caines ............ A61F 2/68 623/26 |
| 5,092,902 A | | 3/1992 | Adams et al. |
| 5,246,465 A | | 9/1993 | Rincoe et al. |
| 5,290,319 A | | 3/1994 | Phillips |
| 5,383,939 A | | 1/1995 | James |
| 5,544,528 A | | 8/1996 | Woyski et al. |
| 5,571,205 A | | 11/1996 | James |
| 5,586,435 A | | 12/1996 | Kokalis |
| 5,810,130 A | | 9/1998 | McCandless |
| 5,888,212 A | | 3/1999 | Petrofsky et al. |
| 5,893,891 A | | 4/1999 | Zahedi |
| 5,921,358 A | | 7/1999 | Gramnas |
| 5,957,981 A | | 9/1999 | Gramnas |
| 6,007,582 A | | 12/1999 | May |
| 6,082,507 A | | 7/2000 | Forster |
| 6,113,642 A | | 9/2000 | Petrofsky et al. |
| 6,427,970 B1 | | 8/2002 | Silva |
| 6,443,993 B1 | | 9/2002 | Koniuk |
| 6,517,585 B1 | | 2/2003 | Zahedi et al. |
| 6,673,117 B1 | | 1/2004 | Soss et al. |
| 6,719,807 B2 | | 4/2004 | Harris |
| 6,740,125 B2 | | 5/2004 | Mosler |
| 6,741,911 B2 | | 5/2004 | Simmons |
| 6,755,870 B1 | | 6/2004 | Biedermann et al. |
| 6,764,520 B2 | | 7/2004 | Deffenbaugh et al. |
| 6,855,170 B2 | | 2/2005 | Gramnas |
| 6,875,241 B2 | | 4/2005 | Christesen |
| 6,902,585 B2 | | 6/2005 | Hikichi |
| 6,910,331 B2 | | 6/2005 | Asai et al. |
| 6,911,050 B2 | | 6/2005 | Molino et al. |
| 7,052,519 B1 | | 5/2006 | Gramnas |
| 7,066,964 B2 | | 6/2006 | Wild |
| 7,279,009 B2 | | 10/2007 | Herr et al. |
| RE39,961 E | | 12/2007 | Petrofsky et al. |
| 7,393,364 B2 | | 7/2008 | Martin |
| 7,485,152 B2 | 2/2009 | Haynes et al. |
| 7,507,259 B2 | 3/2009 | Townsend et al. |
| 7,655,050 B2 | 2/2010 | Palmer et al. |
| 7,691,154 B2 | 4/2010 | Asgeirsson et al. |
| 7,799,091 B2 | 9/2010 | Herr et al. |
| 7,845,370 B2 | 12/2010 | Cook et al. |
| 7,848,058 B2 | 12/2010 | Huang et al. |
| 7,862,622 B2 | 1/2011 | Dunlap et al. |
| 7,883,548 B2 | 2/2011 | Lang |
| 7,942,935 B2 | 5/2011 | Iversen et al. |
| 7,963,998 B2 | 6/2011 | Boiten |
| 7,985,265 B2 | 7/2011 | Moser et al. |
| 8,001,993 B2 | 8/2011 | Cook |
| 8,142,370 B2 | 3/2012 | Weinberg et al. |
| 8,206,458 B1 | 6/2012 | Hawkins |
| 8,444,704 B2 | 5/2013 | Palmer et al. |
| 8,574,312 B2 | 11/2013 | Moser et al. |
| 8,623,098 B2 | 1/2014 | Goldfarb et al. |
| 8,641,780 B2 | 2/2014 | Abimosleh et al. |
| 8,652,218 B2 | 2/2014 | Goldfarb et al. |
| 8,655,808 B2 | 2/2014 | Palmer et al. |
| 8,740,991 B2 | 6/2014 | Moser et al. |
| 8,959,038 B2 | 2/2015 | Palmer et al. |
| 8,986,389 B2 | 3/2015 | Lim et al. |
| 8,986,396 B2 | 3/2015 | Goldfarb et al. |
| 8,986,398 B2 | 3/2015 | Poulson, III et al. |
| 9,028,557 B2 | 5/2015 | Steele et al. |
| 9,180,025 B2 | 11/2015 | Goldfarb et al. |
| 9,289,315 B2 | 3/2016 | Goldfarb et al. |
| 9,289,317 B2 | 3/2016 | Goldfarb et al. |
| 9,750,620 B2 | 9/2017 | Goldfarb et al. |
| 9,763,809 B2 | 9/2017 | Palmer et al. |
| 9,849,002 B2 | 12/2017 | Palmer et al. |
| 2002/0152750 A1 | 10/2002 | Asai et al. |
| 2005/0092952 A1 | 5/2005 | McCarroll et al. |
| 2006/0235544 A1 | 10/2006 | Iversen et al. |
| 2006/0293761 A1 | 12/2006 | Baumann et al. |
| 2007/0050044 A1 | 3/2007 | Haynes et al. |
| 2007/0061016 A1 | 3/2007 | Kuo et al. |
| 2007/0083272 A1 | 4/2007 | Van De Veen et al. |
| 2007/0198098 A1 | 8/2007 | Roston et al. |
| 2008/0097269 A1 | 4/2008 | Weinberg et al. |
| 2008/0099090 A1 | 5/2008 | Cook |
| 2008/0114272 A1 | 5/2008 | Herr et al. |
| 2008/0200994 A1 | 8/2008 | Colgate et al. |
| 2008/0262635 A1 | 10/2008 | Moser et al. |
| 2008/0281435 A1 | 11/2008 | Abimosleh et al. |
| 2008/0300692 A1 | 12/2008 | Moser et al. |
| 2009/0001305 A1 | 1/2009 | Cook et al. |
| 2009/0030530 A1 | 1/2009 | Martin |
| 2009/0054996 A1 | 2/2009 | Sykes et al. |
| 2009/0204230 A1 | 8/2009 | Kaltenborn et al. |
| 2009/0222105 A1 | 9/2009 | Clausen |
| 2009/0259320 A1 | 10/2009 | Andrysek |
| 2009/0299489 A1 | 12/2009 | Gramnaes |
| 2010/0023133 A1 | 1/2010 | Fairbanks et al. |
| 2010/0049334 A1 | 2/2010 | Okuda et al. |
| 2010/0191347 A1 | 7/2010 | Pusch et al. |
| 2010/0292807 A1 | 11/2010 | Velez et al. |
| 2011/0082566 A1 | 4/2011 | Herr et al. |
| 2011/0087339 A1 | 4/2011 | Pusch et al. |
| 2011/0093089 A1 | 4/2011 | Martin |
| 2011/0098828 A1 | 4/2011 | Balboni et al. |
| 2011/0130846 A1 | 6/2011 | Kampas et al. |
| 2011/0197682 A1 | 8/2011 | Palmer |
| 2011/0199101 A1 | 8/2011 | Steele |
| 2011/0202144 A1 | 8/2011 | Palmer et al. |
| 2011/0224803 A1 | 9/2011 | Goldfarb et al. |
| 2011/0264230 A1 | 10/2011 | Herr et al. |
| 2011/0307078 A1 | 12/2011 | Boender |
| 2012/0004736 A1 | 1/2012 | Goldfarb et al. |
| 2012/0130508 A1 | 5/2012 | Harris et al. |
| 2012/0136458 A1 | 5/2012 | Martin |
| 2013/0268090 A1 | 10/2013 | Goldfarb et al. |
| 2013/0310949 A1 | 11/2013 | Goldfarb et al. |
| 2014/0100667 A1 | 4/2014 | Goldfarb et al. |
| 2014/0172120 A1 | 6/2014 | Steele et al. |
| 2014/0277581 A1 | 9/2014 | Steele et al. |
| 2015/0066154 A1 | 3/2015 | Palmer, III et al. |

(56) References Cited

U.S. PATENT DOCUMENTS

| | | | |
|---|---|---|---|
| 2015/0066155 | A1 | 3/2015 | Haque |
| 2015/0209159 | A1 | 7/2015 | Goldfarb et al. |
| 2015/0297364 | A1 | 10/2015 | Goldfarb et al. |
| 2015/0320574 | A1 | 11/2015 | Steele et al. |
| 2015/0359698 | A1* | 12/2015 | Popovic .............. A61H 1/024 623/26 |
| 2016/0242936 | A1 | 8/2016 | Goldfarb et al. |
| 2016/0287414 | A1 | 10/2016 | Goldfarb et al. |
| 2017/0100264 | A1 | 4/2017 | Goldfarb et al. |
| 2017/0333222 | A1 | 11/2017 | Goldfarb et al. |

FOREIGN PATENT DOCUMENTS

| | | |
|---|---|---|
| EP | 0 576 379 A1 | 12/1993 |
| EP | 1 101 461 A1 | 5/2001 |
| GB | 2 138 969 A | 10/1984 |
| GB | 2 367 753 A | 4/2002 |
| JP | 59-183747 A1 | 10/1984 |
| JP | 5336386 B2 | 11/2013 |
| WO | WO-02/15826 A1 | 2/2002 |
| WO | WO-2011/080556 | 7/2011 |

OTHER PUBLICATIONS

Corrected Notice of Allowability dated Aug. 23, 2017, for U.S. Appl. No. 14/466,081, filed Aug. 22, 2014, 4 pages.
Custom Sensor Technologies, Verified by the Wayback Machine Nov. 14, 2012. Kimco Magnetics Voice Coil Actuators Applications and Product Selection Guide, 20 pages.
"Echelon" (Jun. 24, 2013). Located at http://www.endolite.com/products/echelon; Accessed Jun. 24, 2013; 2 Pages.
"Elan," (Jun. 24, 2013). Located at http://www.endolite.com/products/elan; Accessed Jun. 24, 2013; 2 Pages.
"Elan Flyer," (Sep. 2015). Located at http://www.endolite.com/catalogue/feet/new- elan/flyer/en_US/936562%20Elan%20Flyer%20iss5%20US_AW_web.pdf, accessed on Mar. 31, 2016, 4 pages.
Extended European Search Report dated Mar. 21, 2014, for EP Application No. 14 151 179.0, filed on Jan. 14, 2014, 9 pages.
Extended European Search Report dated Apr. 7, 2014, for EP Application No. 14 152 194.8, filed on Jan. 22, 2014, 5 pages.
Extended European Search Report dated Apr. 29, 2015, for EP Application No. 14 182 396.3, filed on Aug. 27, 2014, 9 pages.
Extended European Search Report dated Nov. 24, 2017, for EP Application No. 17 169 149.6, filed on Jan. 22, 2014, 7 pages.
Extended European Search Report dated Jan. 22, 2018, for EP Application No. 17 164 872.8, filed on Aug. 27, 2014, 6 pages.
Final Office Action dated Nov. 21, 2014, for U.S. Appl. No. 13/829,714, filed Mar. 14, 2013, 20 pages.
Final Office Action dated Jan. 12, 2017, for U.S. Appl. No. 14/466,081, filed Aug. 22, 2014, 20 pages.
Freedom Innovations; Plie$^{2.0}$ MPC Knee, trademark of Freedom Innovations, LLC; Natural by Design, 6 pages.
Korane, K. (Jun. 9, 2011). "New surface-inspection techniques improve hydraulic cylinder rods and seals," Machine Design, Penton Media, Inc., 4 pages.
Krips, W. (Jun. 1, 2003). Neue Antriebstechnolgie bei hochdynamischen Stetigwegeventilen; O+ P Olhydraulik und Pneumatik 47(6):3, Vereinigte Fachverlage; Mainz, DE; Article submitted with Parker Press Report DF Plus which reports on the technology contained in the German article, 8 total pages (with English Translation).
Laurenson (Feb. 1985). "The Design of Self-Centering Seal-Less Hydraulic Pistons," *Journal of Engineering Manufacture* 199(1):59-65 (English abstract only).
Non-Final Office Action dated Jul. 18, 2014, for U.S. Appl. No. 13/829,714, filed Mar. 14, 2013, 22 pages.
Non-Final Office Action dated Aug. 8, 2014, for U.S. Appl. No. 13/793,892, filed Mar. 11, 2013, 16 pages.
Non-Final Office Action dated Nov. 4, 2015, for U.S. Appl. No. 14/466,122, filed Aug. 22, 2014, 18 pages.
Non-Final Office Action dated May 5, 2016, for U.S. Appl. No. 14/466,081, filed Aug. 22, 2014, 16 pages.
Non-Final Office Action dated Aug. 29, 2016, for U.S. Appl. No. 14/466,122, filed Aug. 22, 2014, 13 pages.
Non-Final Office Action dated May 17, 2017, for U.S. Appl. No. 14/707,957, filed May 8, 2015, 23 pages.
Notice of Allowance dated Jan. 20, 2015, for U.S. Appl. No. 13/793,892, filed Mar. 11, 2013, 7 pages.
Notice of Allowance dated Feb. 17, 2015, for U.S. Appl. No. 13/793,892, filed Mar. 11, 2013, 4 pages.
Notice of Allowance dated May 3, 2017, for U.S. Appl. No. 14/466,081, filed Aug. 22, 2014, 8 pages.
Notice of Allowance dated on Apr. 1, 2015, for U.S. Appl. No. 13/829,714, filed Mar. 14, 2013, 8 pages.
Notice of Allowance dated Aug. 16, 2017, for U.S. Appl. No. 14/466,122, filed Aug. 22, 2014, 5 pages.
Parker, "Fluid Power Seal Design Guide", Nov. 12, 2012, copyright date 2003, 8 pages.
Partial European Search Report dated Dec. 19, 2014, for EP Application No. 14 182 396.3, filed on Aug. 27, 2014, 6 pages.
Shields et al. (2006). Design, Control, and Energetic Characterization of a Solenoid Injected Monopropellant Powered Actuator; IEEE/ASME Transactions on Mechatronics 11(4):477-487.
Weingarten, F. (2004). Hyraulikosungen fur Produktions machinen; O+ P Olhydraulik and Pneumatik 48(9):1-2, Vereinigte Fachverlage; Mainz, DE. (with English Abstract).
Extended European Search Report received in EP Application No. 19160401.6 dated Aug. 29, 2019.
Krips, Walter , "Neue Antriebstechnologie Bei Hochdynamischen Stetigwegenventilen", O + P Olhydraulik Und Pneumatik, Vereinigte Fachverlage, Mainz, DE, vol. 47, No. 6, Jun. 1, 2003, XP001185024, ISSN: 0341-2660, p. 3, col. 1.
Weingarten, Franz, "Hydraulikloesungen Fuer Produktionsmaschinen Neue Rgelventile Und-Antriebe Eroeffenen Neue Moglichkeiten" , O + P Olhydraulik Und Pneumatik, Vereinigte Fachverlage, Mainz, DE, Sep. 1, 2004, pp. 560-565, XP001210692, ISSN: 0341-2660, p. 1,2.

* cited by examiner

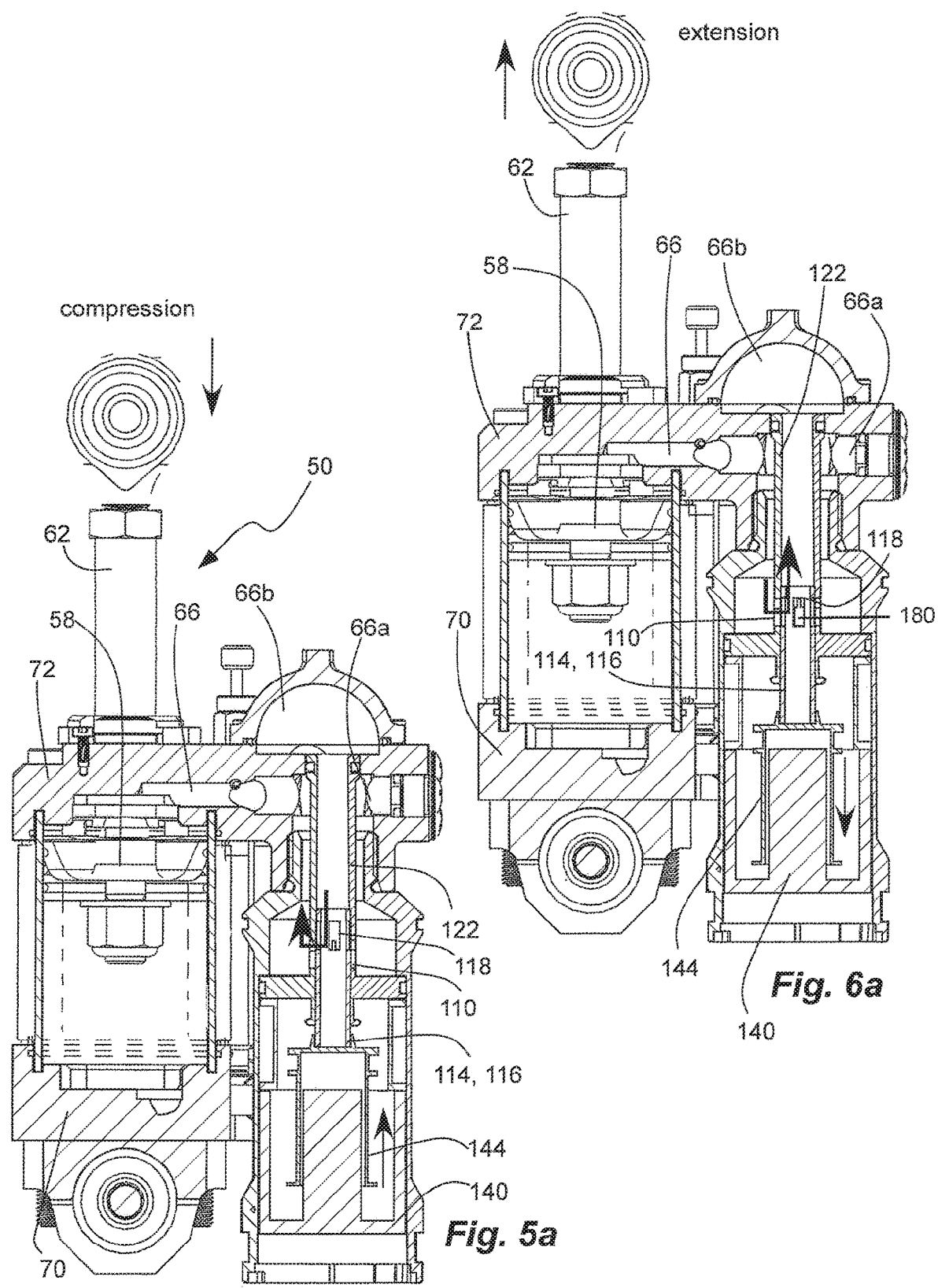

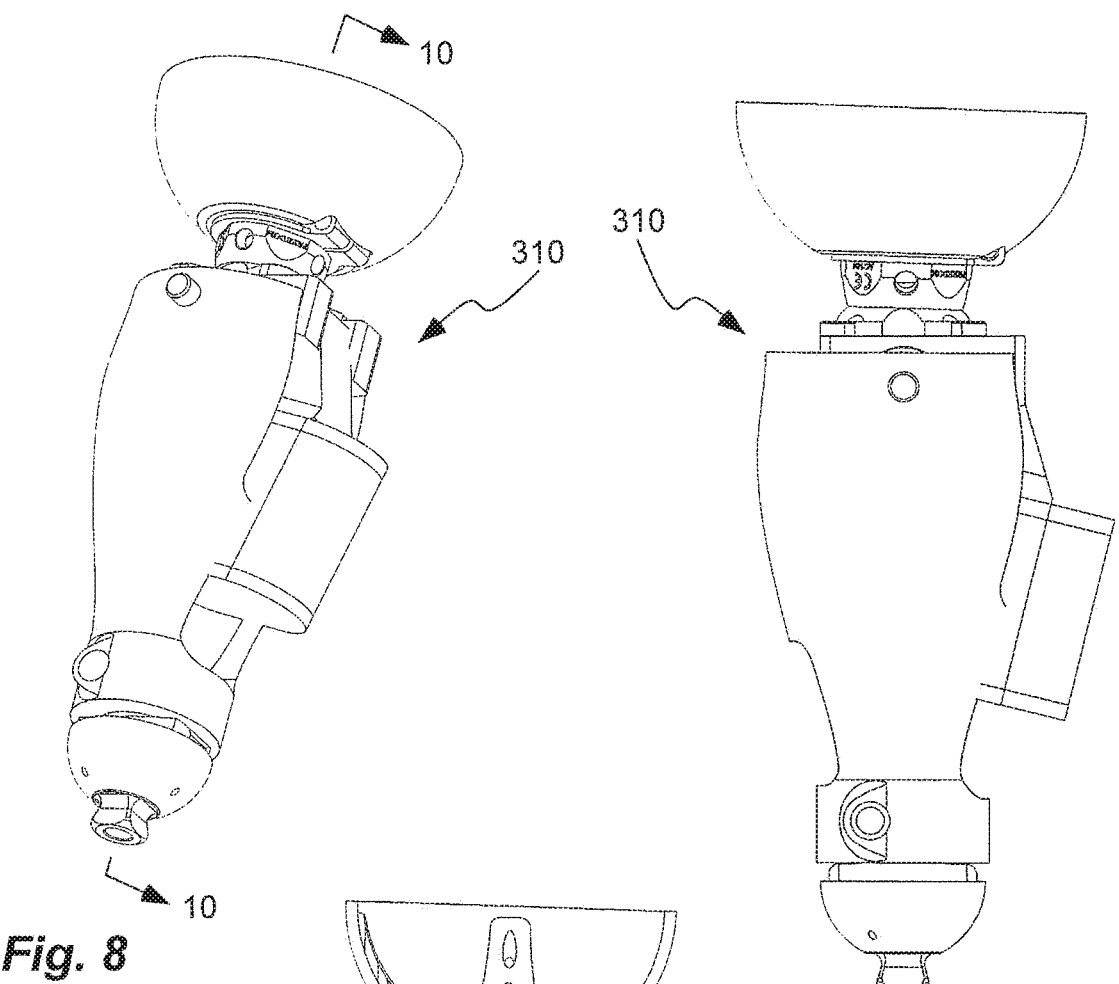
*Fig. 8*
*Fig. 9*
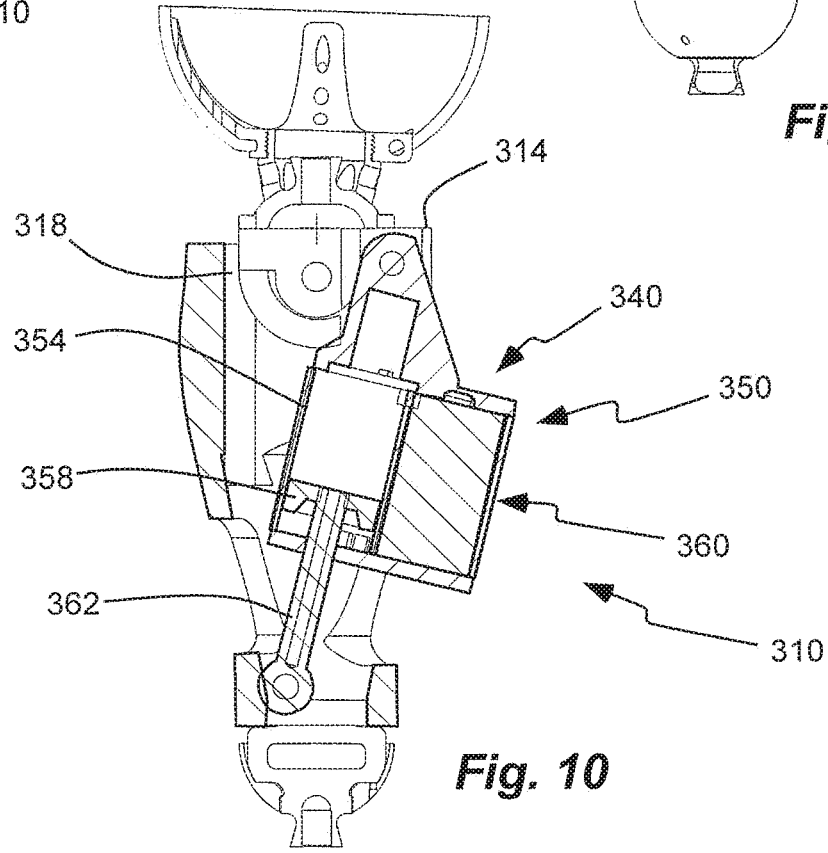
*Fig. 10*

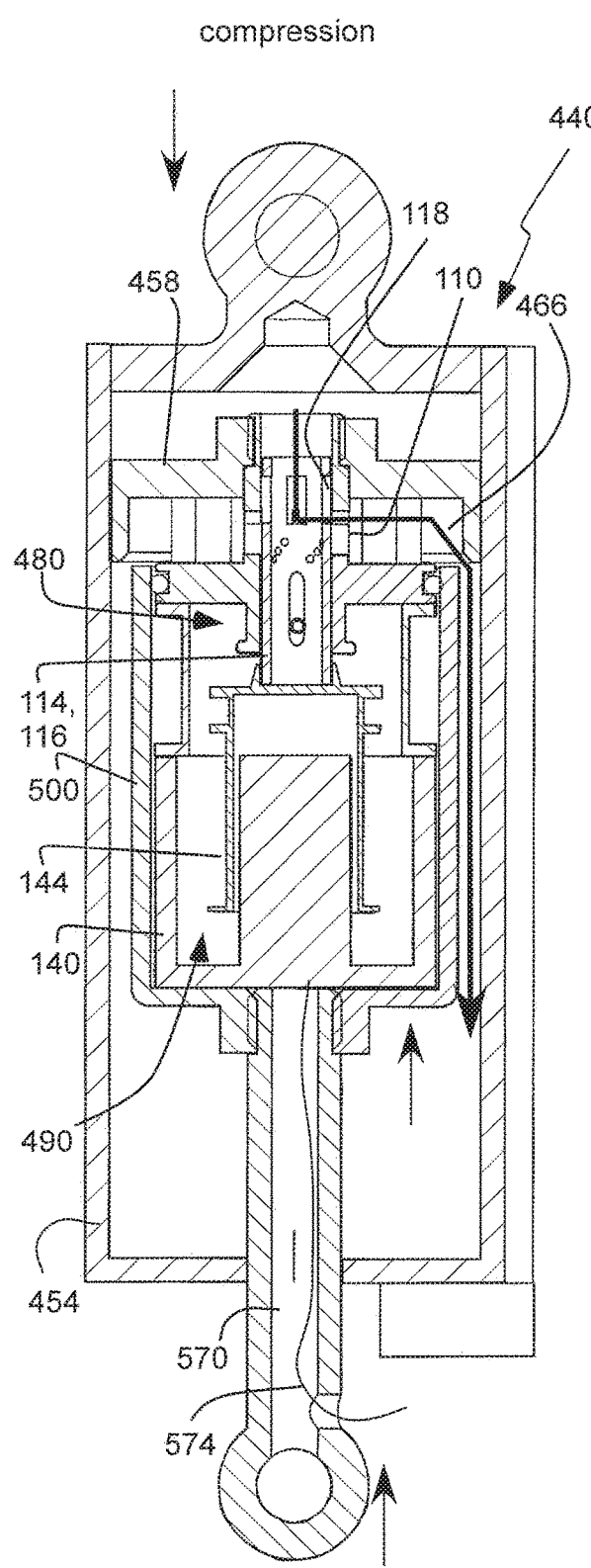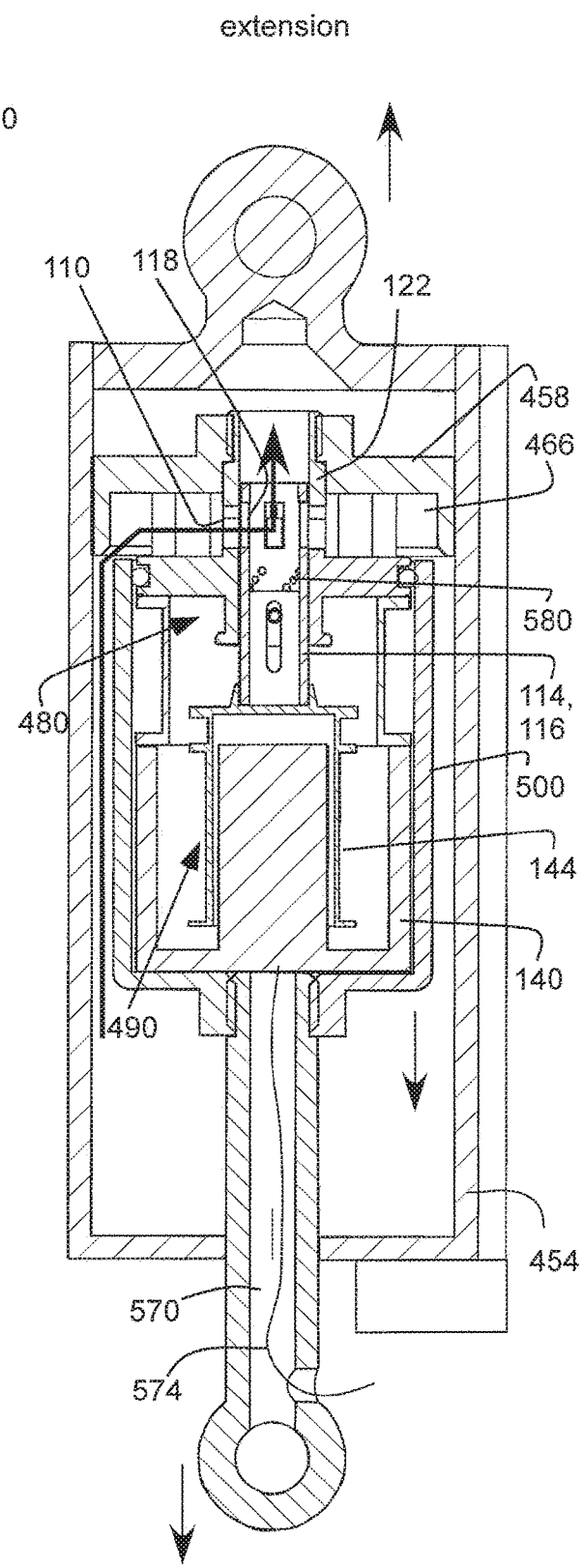
*Fig. 13a*  *Fig. 14a*

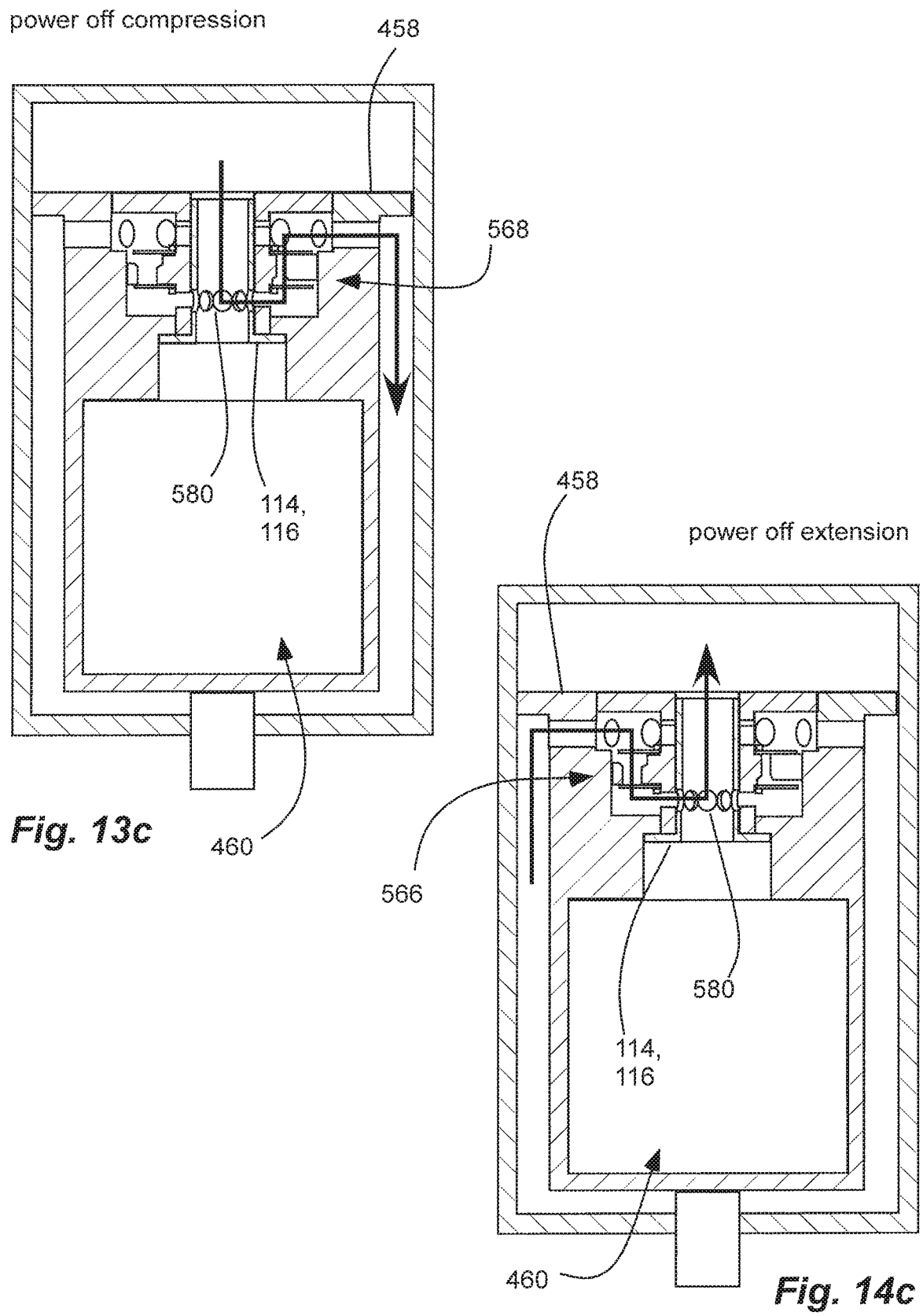

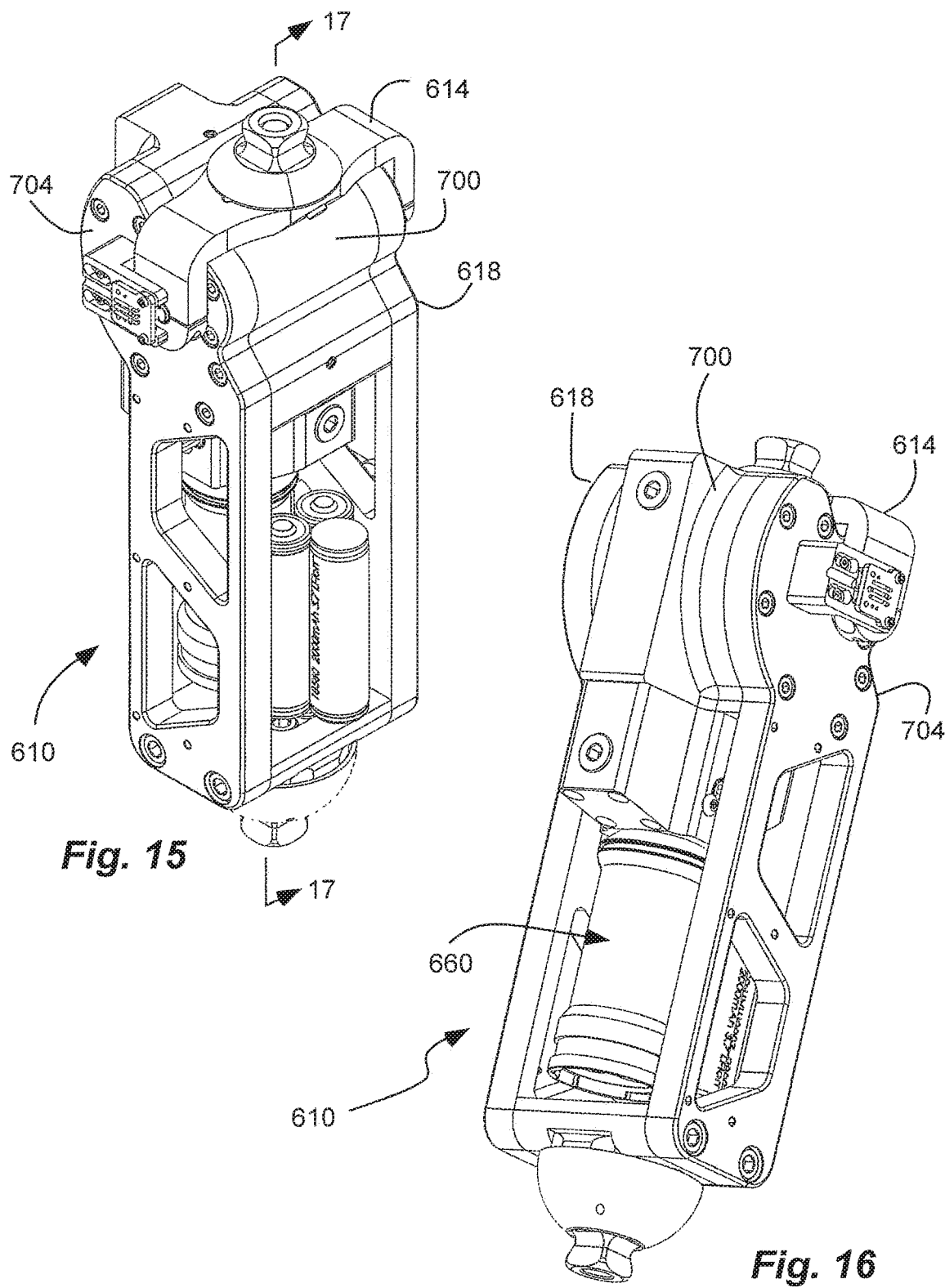

PROSTHETIC WITH VOICE COIL VALVE

PRIORITY CLAIM(S)

This is a continuation of U.S. patent application Ser. No. 14/707,957, filed on May 8, 2015, which is a continuation of U.S. patent application Ser. No. 13/829,714, filed on Mar. 14, 2013, now U.S. Pat. No. 9,028,557, each of which is hereby incorporated herein by reference.

BACKGROUND

Field of the Invention

The present invention relates generally to prosthetics with a hydraulic damper or actuator. More particularly, the present invention relates to a prosthetic knee.

Related Art

The development of a prosthetic knee with a more natural function or gait is an ongoing endeavor. Examples of prosthetic knees include U.S. Pat. No. RE39,961 (U.S. Pat. No. 6,113,642) and U.S. Pat. No. 7,655,050; and the Plie® prosthetic knee by Freedom Innovations, Inc.

Prosthetic knees often incorporate a hydraulic damping scheme to limit or control movement about the knee. The hydraulic damping systems often utilize a solenoid valve to limit or resist the flow of hydraulic fluid. A solenoid valve is typically on or off, and can typically operate by drawing a plunger into an activated magnetic coil and against a spring, which spring can return the plunger when the coil is deactivated. In addition, some hydraulic damping systems may also, or in the alternative, utilize a stepper motor.

Prior art prosthetic knees often do not meet the advanced demands needed by today's amputee.

SUMMARY OF THE INVENTION

It has been recognized by the inventors of the present invention that prior art solenoid valves in hydraulic prosthetics lack an ability to finely adjust rates of fluid flow; and that prior art stepper motor control valves in hydraulic prosthetics lack response time to control fluid in both directions, often resulting in parallel systems with double the weight and complexity. It has been recognized by the inventors of the present invention that it would be advantageous to develop a prosthesis, and namely an above knee prosthesis or prosthetic knee, and/or a hydraulic damper or actuator for such prosthesis, and/or a control valve for such a prosthesis or hydraulic system, that provides bi-directional positioning, proportional control, rapid response and/or low power consumption. In addition, it has been recognized by the inventors of the present invention that it would be advantageous to develop a prosthesis, and namely an above knee prosthesis or prosthetic knee, and/or a hydraulic damper or actuator for such prosthesis, and/or a control valve for such a prosthesis or hydraulic system, that provides two different regions of linear proportional control.

In addition, it has been recognized by the inventors of the present invention that it would be advantageous to incorporate a voice coil valve, rather than a solenoid valve, into a prosthetic knee, and to address the prior size concerns that such a voice coil valve may raise. Furthermore, it has been recognized by the inventors of the present invention that a voice coil valve can provide reciprocal or bidirectional movement based on the polarity of an applied current (as opposed to the unidirectionally driven movement in that the armature of a solenoid that only moves in one direction regardless of the polarity of the current applied, and that requires a spring for return movement). The inventors further recognized that the force produced by the voice coil actuator is proportional (and substantially linear) to the current applied (and the velocity of the coil is proportional to the voltage applied), unlike a solenoid (with non-linear time and force response, and higher power consumption towards one end of the stroke due to the need of constantly working against the return spring force). Thus, the actuator has a substantially linear time and force response. The movement and force of the voice coil motor is based on the Lorentz Force principle and equation, unlike a spring returned solenoid.

The invention provides a prosthetic with a pair of prosthetic members movably coupled together to allow movement of the pair of prosthetic members with respect to one another. In one aspect, the prosthetic can be a prosthetic knee. A hydraulic actuator or damper includes hydraulic fluid in a hydraulic chamber coupled to one of the pair of prosthetic members, and a hydraulic piston movably disposed in the hydraulic chamber coupled to another of the pair of prosthetic members. A hydraulic flow channel is fluidly coupled between opposite sides of the chamber to allow hydraulic fluid to move between the opposite sides of the chamber as the hydraulic piston moves therein. A voice coil valve is coupled to the hydraulic flow channel to vary resistance to flow of hydraulic fluid through the flow channel, and thus movement of the piston in the chamber, and thus influencing a rate of movement of the pair of prosthetic members with respect to one another.

The voice coil valve can reciprocally and selectively position a valve, or spool thereof, in a bidirectional movement based on the polarity of the current applied to the voice coil. Thus, the valve can be bi-directionally driven in back and forth directions, and bi-directionally positioned. The amount of current can be selected and varied to selectively position a coil with respect to a magnet. The polarity of the current can be selected and changed to select and change the direction of travel of the valve or spool. The force produced by the voice coil valve is proportional (and substantially linear) to the current applied (and the velocity of the coil is proportional to the voltage applied), unlike a solenoid (with non-linear time and force response). Thus, the voice coil valve has a substantially linear time and force response. The movement and force of the voice coil is based on the Lorentz Force principle and equation, unlike a solenoid. In addition, the direction of movement of the coil can be selected, driven and varied by selecting and varying the polarity of the current, unlike a solenoid (which has the same direction of travel irrespective of polarity; i.e. changing the polarity of a solenoid does not alter the direction of induced motion). Thus, the direction of travel of the coil is based on the polarity of the current. The voice coil valve has a rapid response rate (i.e. greater than 100 cycles per second), and a low power consumption (i.e. less than 1.8 Watts, or 150 mAmps @ 12V), unlike a solenoid.

In addition, the invention provides a prosthetic with a pair of prosthetic members movably coupled together to allow movement of the pair of prosthetic members with respect to one another. A hydraulic actuator or damper includes hydraulic fluid in a hydraulic chamber coupled to one of the pair of prosthetic members, and a hydraulic piston movably disposed in the hydraulic chamber and coupled to another of the pair of prosthetic members. The hydraulic piston divides the chamber into opposite sides. A hydraulic flow channel is fluidly coupled between the opposite sides of the chamber to allow hydraulic fluid to move between the opposite sides of the chamber as the hydraulic piston moves therein. A hydraulic valve is operatively coupled in the hydraulic flow channel and includes an orifice and a spool movable with respect to one another to selectively resist flow of the hydraulic fluid through the orifice. The prosthetic includes an electric actuator to move the orifice and the spool with respect to one another. The actuator includes a permanent magnet and a coil movable with respect to one another, and reciprocally positionable with current polarity induced, bi-directional movement, by selectively changing a polarity of electric current applied to the electric actuator, such that the spool is selectively positioned and bi-directionally driven in back and forth directions, such that the hydraulic valve varies resistance to the flow of hydraulic fluid through the flow channel. The actuator has a substantially linear time and force response with a rapid response rate, capable of greater than 100 cycles per second, and a low power consumption less than 1.8 Watts. The valve has a pair of different, substantially linear control regions including: a first region providing a region of control during slow extension/retraction of the hydraulic actuator or damper between 1.5 to 2.5 inches per second, and a second region providing a region of control during fast extension/retraction of the hydraulic actuator or damper between 6 to 8 inches per second.

Furthermore, the invention provides a prosthetic knee for an above knee amputee with pair of prosthetic members including a thigh link configured to be coupled to a remnant limb of the amputee, and pivotally coupled to a shank link configured to be coupled to an artificial foot. The thigh link and shank link are pivotally coupled together at a primary pivot to allow flexion and extension of the shank link with respect to the thigh link. A hydraulic actuator or damper includes hydraulic fluid in a hydraulic chamber coupled to one of the pair of prosthetic members, and a hydraulic piston movably disposed in the hydraulic chamber and coupled to another of the pair of prosthetic members. The hydraulic piston divides the chamber into opposite sides. A hydraulic flow channel is fluidly coupled between the opposite sides of the chamber to allow hydraulic fluid to move between the opposite sides of the chamber as the hydraulic piston moves therein. A voice coil valve is coupled to the hydraulic flow channel to vary resistance to flow of hydraulic fluid through the flow channel, and thus movement of the piston in the chamber, and thus pivoting of the pair of prosthetic members with respect to one another. The voice coil valve includes: an orifice and a spool movable with respect to one another to selectively resist flow of the hydraulic fluid through the orifice; and a permanent magnet and a coil, coupled to the valve to move the orifice and the spool with respect to one another, and movable with respect to one another, and reciprocally positionable with current polarity induced, bi-directional movement, by selectively changing a polarity of electric current applied to the electric actuator, such that the spool is selectively positioned and bi-directionally driven in back and forth directions, such that the hydraulic valve selectively varies resistance to the flow of hydraulic fluid through the flow channel. The voice coil valve has a rapid response rate, capable of greater than 100 cycles per second, and a low power consumption less than 1.8 Watts.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 5a is a cross-sectional schematic view of the hydraulic system of FIG. 4, shown in cylinder compression or knee flexion;

FIG. 6a is a cross-sectional schematic view of the hydraulic system of FIG. 4, shown in cylinder extension or knee extension;

FIG. 8 is a perspective view of another prosthetic knee in accordance with another embodiment of the present invention showing a different embodiment of a packaging solution for a control valve or voice coil valve;

FIG. 9 is a side view of the prosthetic knee of FIG. 8;

FIG. 10 is a cross-sectional side view of the prosthetic knee of FIG. 8, taken along line 10-10 in FIG. 8;

FIG. 13a is a cross-section side schematic view of a hydraulic actuator or damper, or hydraulic system, of the prosthetic knee of FIG. 11, show in compression or flexion;

FIG. 13c is a schematic cross-sectional side view of the control valve or voice coil valve of FIG. 11 with enhanced power off functionality, shown in cylinder compression or knee flexion and metering in a non-powered state;

FIG. 14a is a cross-section side schematic view of a hydraulic actuator or damper, or hydraulic system, of the prosthetic knee of FIG. 11, show in cylinder extension and knee extension;

FIG. 14c is a schematic cross-sectional side view of the control valve or voice coil valve of FIG. 11, shown in cylinder extension and knee extension and in a non-powered state;

FIG. 15 is a perspective view of another prosthetic knee in accordance with another embodiment of the present invention showing a rotary vane hydraulic system;

FIG. 16 is another perspective view of the prosthetic knee of FIG. 15;

Figure 1:
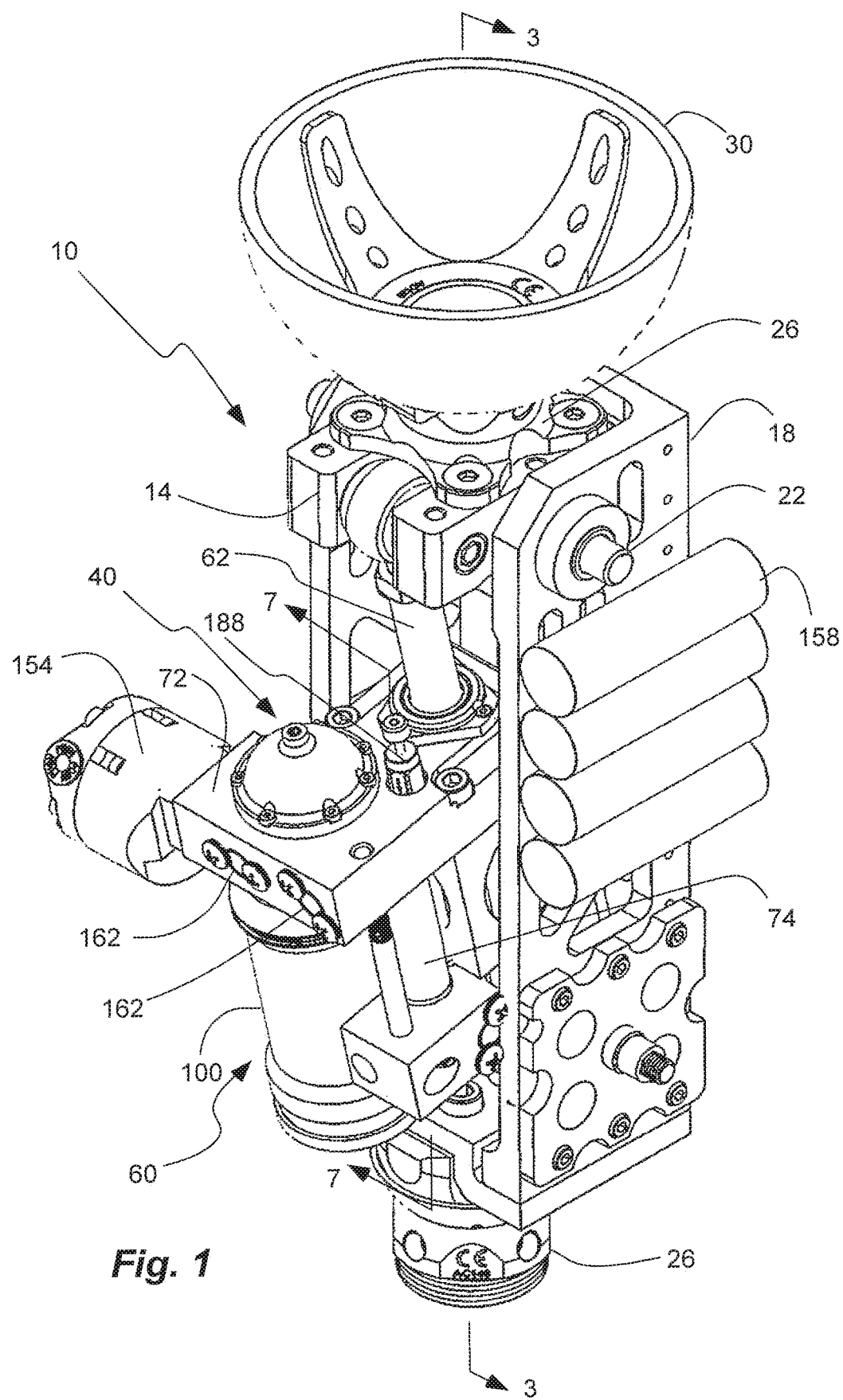
FIG. 1 is a perspective view of a prosthetic knee in accordance with an embodiment of the present invention.
Figure 2:
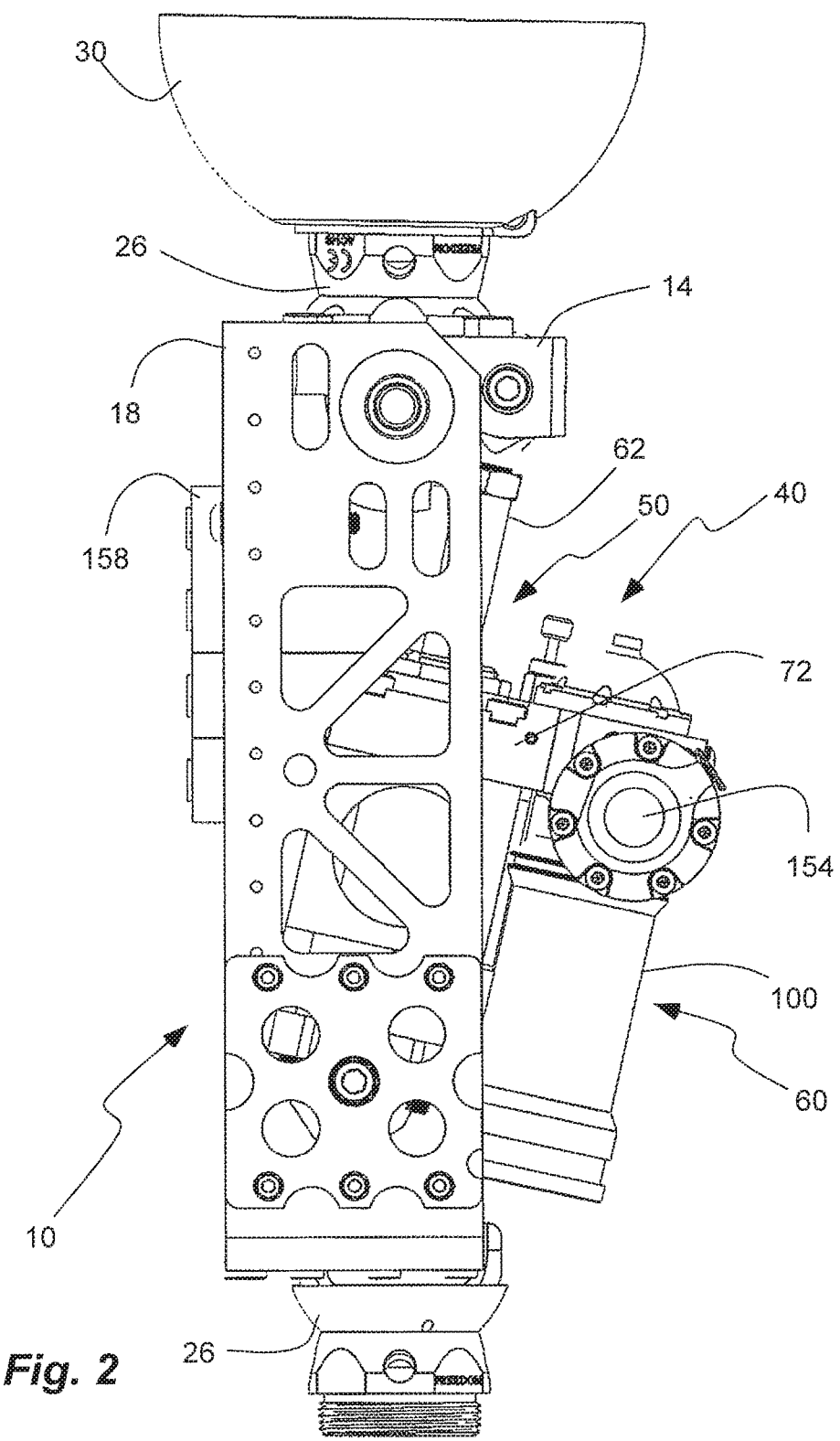
FIG. 2 is a side view of the prosthetic knee of FIG. 1.
Figure 3:
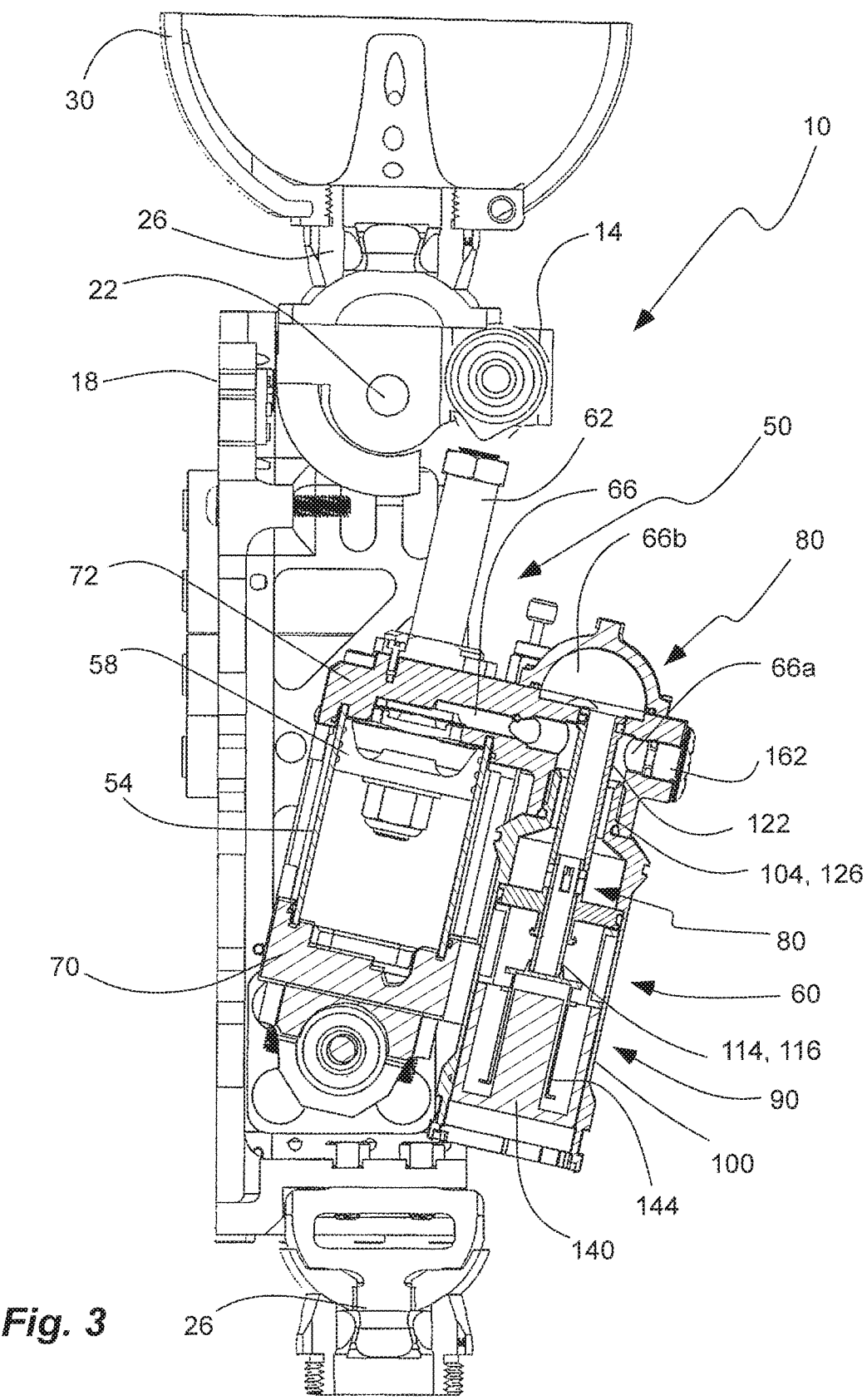
FIG. 3 is a cross-sectional side view of the prosthetic knee of FIG. 1, taken along line 3-3 in FIG. 1.
Figure 4:
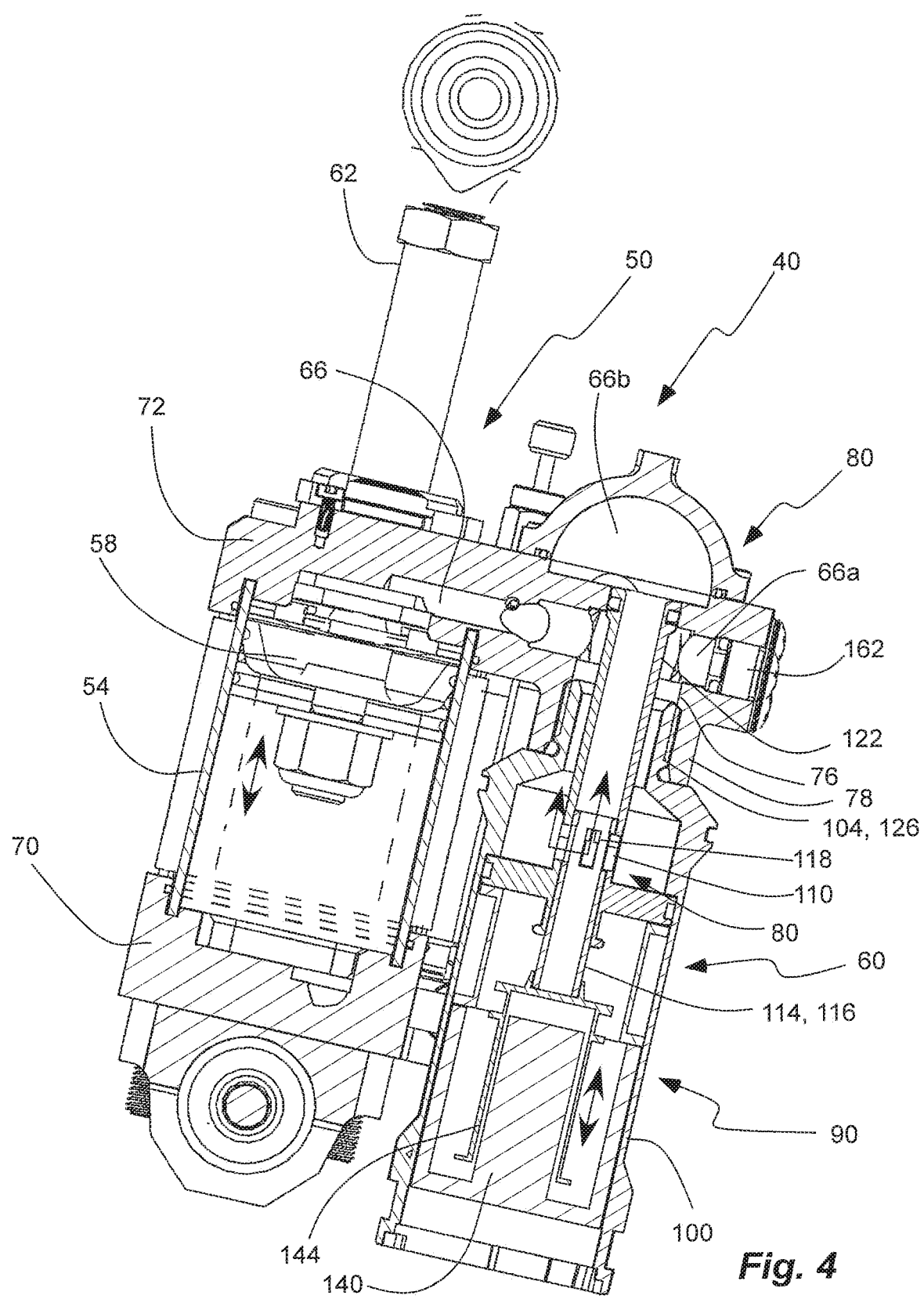
FIG. 4 is a cross-sectional side view of a hydraulic system of the prosthetic knee of FIG. 1.

In the above mentioned figures, hydraulic fluid has been removed for visibility of the components. Although the hydraulic fluid is not shown, those skilled in the art will clearly understand the volumes it occupies, and the channels it flows through.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

The invention provides a prosthetic device for use by an amputee. The prosthetic device is shown herein configured as a prosthetic knee for use by an above-knee amputee. The prosthetic device of the present invention can be configured as other prosthetics and/or for use in other locations. For example, the prosthetic device can be configured for use as a prosthetic ankle for a below-knee amputee, or an above-knee amputee.

The prosthetic device or prosthetic knee can have a pair of prosthetic members that are movably and/or pivotally coupled to one another, and move and/or pivot with respect to one another. For example, the pair of prosthetic members can move in flexion and extension in the case of a prosthetic knee. In addition, the prosthetic members can move in dorsiflexion and plantar-flexion in the case of a prosthetic ankle. The prosthetic members can move and/or pivot about a single pivot joint or axle, or across a locus of points such as in a multi-bar linkage, or other type of linkage.

A hydraulic actuator or damper can also be coupled to and between the pair of prosthetic members to control or limit the movement and/or pivoting between the members. The terms "hydraulic actuator", "hydraulic damper" and "hydraulic actuator or damper" are used interchangeably herein to refer to a hydraulic system that imposes some type of limitation or control on the movement of a hydraulic fluid, and thus some type of limitation or control on the relative movement between the prosthetic members. The hydraulic system can be a hydraulic damper that simply limits or resists movement of the hydraulic fluid, and thus simply limits or resists movement between the pair of prosthetic members. The hydraulic system can be a hydraulic actuator that includes a hydraulic motor that drives or creates hydraulic pressure to drive movement between the pair of prosthetic members. Such a hydraulic actuator can also be operated as a damper.

The hydraulic system can include a hydraulic separator, such as a piston or vane, movable in a hydraulic chamber, such as a cylinder or rotary chamber, to displace hydraulic fluid from one side of the working chamber to the other. The piston can be coupled to one of the prosthetic members, while the chamber is coupled to the other of the prosthetic members in the embodiment of a linear piston damper, or in the embodiment of a rotary piston damper. Such couplings can be secondary pivotal couplings, separate from a primary pivot between the pair of members. The piston can divide the chamber into opposite sides and the hydraulic system can be configured to displace the fluid from one side of the piston to the other, or from one side of the chamber to the other. Thus, the hydraulic system can have a hydraulic flow channel fluidly coupled between the opposite sides of the chamber to allow the hydraulic fluid to move between the opposite sides of the chamber as the piston moves therein. In one aspect, the hydraulic system can include an overflow reservoir to accommodate the different volumes of the opposite sides of the chamber due to the volume of piston rod coupled to the piston. In another aspect, the hydraulic system can include a piston rod on both sides of the piston, which exits the working chamber on both sides, commonly termed a "thru-rod" damper, so that the sum of the volume on both sides of the chamber during the stroke remains constant.

A control valve can be coupled to the hydraulic flow channel to vary resistance to the hydraulic fluid flow or vary the flow rate. Prior art solenoid valves have been used to vary flow. Solenoid valves typically have a stationary iron core with a coil, and a movable iron armature that is moved when current is applied to the coil. Solenoid valves also typically rely on a spring for return movement when the current is removed from the coil. Thus, solenoid valves often have an on-off operation. Solenoid valves generate force proportional to the square of the current (and are thus non-linear). Solenoids are relatively inexpensive. It has been recognized by the inventors, however, that solenoid valves are or can be limited by unidirectionally driven movement in that the armature only moves in one direction regardless of the polarity of the current applied, and that a spring is required for return movement. In addition, it has been recognized by the inventors that solenoid valves are or can be limited by requiring additional current to overcome the spring force of the spring, thus requiring greater power consumption. In addition, it has been recognized by the inventors that solenoid valves are or can be limited by slower response times and/or non-linear response time (and force).

The inventors have recognized that the control valve can include an electric actuator, coupled to a hydraulic valve, to reciprocally and selectively position the valve, or spool thereof, in a bidirectional movement based on the polarity of the current applied to the actuator. Thus, the valve can be bi-directionally driven in back and forth directions, and bi-directionally positioned. The electric actuator includes a permanent magnet and a coil movable with respect to one another. The permanent magnet can have a magnetic field in which the coil moves when a current is applied to the coil. As well, the same response can be generated when the magnet moves, and the coil remains stationary, when electricity is used. The amount of current can be selected and varied to selectively position the coil with respect to the magnet. The polarity of the current can be selected and changed to select and change the direction of travel of the coil with respect to the magnet. The force produced by the actuator is proportional (and substantially linear) to the current applied (and the velocity of the coil is proportional to the voltage applied), unlike a solenoid (with non-linear time and force response). Thus, the actuator has a substantially linear time and force response. The movement and force of the voice coil motor is based on the Lorentz Force principle and equation, unlike a solenoid. In addition, the direction of movement of the coil can be selected, driven and varied by selecting and varying the polarity of the current, unlike a solenoid (which has the same direction of travel irrespective of polarity; i.e. changing the polarity of a solenoid does not alter the direction). Thus, the direction of travel of the coil is based on the polarity of the current. The actuator, and thus the valve, has a rapid response rate (i.e. greater than 100 cycles per second), and a low power consumption (i.e. less than 1.8 Watts, or 150 mAmps @ 12V), unlike a solenoid. Such an actuator or valve can be referred to as a voice coil or voice coil valve. The actuator is coupled to the hydraulic flow valve, which is operatively coupled in the hydraulic flow path. The valve includes an orifice and a spool movable with respect to one another. The actuator is coupled to the valve to move the orifice and the spool with respect to one another to selectively resist flow of the hydraulic fluid through the orifice. In one aspect, the actuator can move the spool with respect to the orifice. Thus, the hydraulic valve selectively varies the resistance of the hydraulic valve to the flow of hydraulic fluid through the flow channel.

The control valve and electrical actuator thereof can be operatively coupled, or electrically coupled or wirelessly coupled, to control electronics, such as a circuit board with a microprocessor, forming a computer to control the control valve, and thus the hydraulic system or hydraulic actuator or damper. The computer can control the hydraulic valve to vary the flow rate of the hydraulic fluid, and thus the resistance to bending, of the knee. The computer can vary the compression and extension of the hydraulic system or hydraulic actuator or damper during the gait cycle of a prosthetic knee; and thus control the compression and extension of the prosthetic knee during gait. The computer and the control valve can vary the resistance and the flow rate of the compression and/or extension of the hydraulic system during both compression and extension of the prosthetic knee or members thereof.

As illustrated in FIGS. 1-7, a prosthetic device, namely a prosthetic knee, indicated generally at 10, is shown in an example implementation in accordance with an embodiment of the invention. The prosthetic knee 10 includes a pair of prosthetic members, namely an upper member or rotor or thigh link 14, and a lower member or frame or shank link 18, that are pivotally coupled together at a primary pivot 22. The upper and lower members 14 and 18, or components thereof, can be machined or cast from metal, such as aluminum, and/or injection molded from plastic. The primary pivot 22 can include an axle and bearings. The upper member 14 can be disposed at a location of a natural knee, while the lower member 18 can extend along a length of a natural shin or lower leg. Both members 14 and 18 can have connectors 26 at distal ends thereof, such as pyramid connectors as known in the art, for attachment to a socket 30 and a prosthetic foot and/or ankle (not shown), respectively. The socket can be attached to a remnant limb of the amputee. Such sockets, connectors, feet and ankles are known in the art. In use, the lower member can move with respect to the upper member in flexion and extension. The lower member 18 can have an exterior frame or exoskeleton that partially surrounds an interior between the lower connector and the primary pivot, and that is open or partially open in a rearward direction, or has an open rear. The exoskeleton can carry a power supply (such as batteries), control electronics such as a circuit board with a microprocessor, etc.

The prosthetic knee 10 also has a hydraulic system 40 that can include a hydraulic actuator or damper 50 and a control valve 60. The hydraulic system 40 is coupled between the upper and lower members 14 and 18. The hydraulic actuator or damper 50 includes a hydraulic chamber, namely a hydraulic cylinder 54, pivotally coupled to the lower member 18, and a piston 58 with a piston rod 62 pivotally coupled to the upper member 14. The pivotal connections between the hydraulic actuator or damper and the upper and lower members form secondary pivots, separated from the primary pivot. In another aspect, the coupling of the hydraulic actuator or damper can be reversed, with the cylinder coupled to the upper member and the piston rod coupled to the lower member (as shown in FIGS. 8-10). The piston 58 can be cylindrical and can slidably move within the cylinder 54. In addition, the piston 58 divides the cylinder 54 or chamber into opposite sides. The cylinder 54 can be formed by a cylinder disposed between opposite caps 70 and 72, one of which is a lower cap 70 that is pivotally coupled to the lower member 18 (with an axle and bearings), and the other of which is an upper cap 72 that has an aperture to slidably receive the piston rod 62. The piston rod 62 is pivotally coupled to the upper member 14 (with an axle and bearings).

In addition, the linear piston damper system (or piston 58 and cylinder 54) can utilize tightly toleranced components which eliminate the need for elastomeric seals to separate the sides of the hydraulic chamber. By using a "metal-on-metal" fit between the piston and cylinder, the seal drag (or stiction) which would be transferred to the amputee as a jarring or disjointed feeling, can be entirely removed from the system, or greatly reduced. The precision that can be required to form a hydraulic working chamber capable of locking without weeping can require a gap between the acting surfaces of the piston and cylinder on the order of 0.005 mm (0.0002 in). Furthermore, the surface finish that can required to facilitate smooth actuation on both surfaces of the piston and cylinder can be between 0.20 to 0.41 μm (8 to 16 μin) Ra finish.

Hydraulic fluid (not shown for clarity of the components) can fill the cylinder 54 or chamber, and can be displaced from one side of the cylinder 54 or chamber (or piston 58) to the other as the piston 58 moves therein. A hydraulic flow channel 66 is fluidly coupled between the opposite sides of the cylinder 54 or chamber (or piston 58) to allow the hydraulic fluid to move or displace between the opposite sides of the cylinder 54 or chamber (or piston 58) as the piston 58 moves therein. One or more channels can be formed in the caps 70 and 72 to form a portion of the hydraulic flow channel 66. A tube 74 (FIG. 7) can be fluidly coupled to and can extend between the caps 70 and 72 to interconnect the channels in the caps, and also to form a portion of the hydraulic flow channel 66. The upper cap 72 can have a channel extending from an upper chamber or upper portion of the cylinder 54, while the lower cap 70 can have a channel extending from a lower chamber or lower portion of the cylinder 54. In addition, the tube 74 can couple the channel from the lower cap 70 to the upper cap 72 or channel thereof. Thus, the upper cap 72 can form and can define a manifold with at least a portion of the hydraulic flow channel 66 formed therein. Within the upper cap 72 or manifold, the hydraulic channel 66 can have a proximal portion 66a and a distal portion 66b (the proximal and distal positions being relative to the control valve 60). A bore 76 can be formed in the upper cap 72 or manifold, and can extend through the proximal portion 66a of the hydraulic channel 66 to the distal portion 66b. An annular flange or mount 78 can extend from the upper cap 72 or manifold, and can circumscribe the bore 76, and can form a portion of the bore.

As indicated above, the prosthetic knee 10 and the hydraulic system 40 include a control valve 60 coupled to the hydraulic flow channel 66 to vary resistance to flow of hydraulic fluid through the flow channel, and thus movement of the piston 58 in the chamber 54, and thus influence a rate of movement of the pair of prosthetic members 18 and 18 with respect to one another. As discussed above, the control valve 60 includes a hydraulic valve 80 that directly contacts and acts upon the hydraulic fluid, and an actuator 90 that drives and controls the hydraulic valve 80. The hydraulic valve 80 and the actuator 90 can be fixed together as a single, operable unit, i.e. the control valve 60, that can be coupled to and carried by the hydraulic system 40, and the hydraulic actuator or damper 50. Thus, the control valve 60 can be removed and replaced as a single unit to facilitate repair or custom applications. The control valve 60 can have, and the hydraulic valve 80 and the actuator 90 can share, a housing or cartridge 100 that can have a fitting 104, such as screw threads, that engage and attach the housing 100 to the cap 72 or manifold, such as at the annular flange or mount 78. The flange or mount 78 and/or bore 76 can include screw threads to receive the fitting 104 of the housing. Thus, the upper cap 72 or manifold receives and carries the control valve 60, and the hydraulic valve 80 and the actuator 90. In addition, the control valve 60 is coupled to the bore 76, and the portions 66a and 66b of the hydraulic channel 66.

The hydraulic valve 80 of the control valve 60 is operatively coupled in the hydraulic flow path or channel 66, and includes at least one orifice 110 and a spool 114 movable with respect to one another to selectively resist flow of the hydraulic fluid through the orifice. The spool 114 can be selectively positioned with respect to the orifice(s) 110 to selectively increase and decrease a cross-sectional area through which the hydraulic fluid can flow. The spool 114 can be or can include a sliding tube 116, and can have a distal end or at least one distal opening 118 that is selectively positionable with respect to the orifice 110. The distal opening 118 can be formed in a sidewall of the sliding tube 116, or the open end thereof, or can be the open end or annular edge thereof. The orifice(s) 110 can be formed in an inner tube 122 circumscribing the sliding tube 116 or spool 114. The spool 114 or sliding tube 116 can slide within the inner tube 122. Thus, the spool 114 or sliding tube 116 can be selectively positioned by the actuator to selectively position the orifice(s) 110 and opening(s) 118 with respect to one another, and selectively increase and decrease a cross-sectional area through which the hydraulic fluid can flow. An outer diameter of the sliding tube 116 can match an inner diameter of the inner tube 122 so that the tubes seal with respect to one another. In another aspect, a distal end or annular edge of the sliding tube or spool can be positioned with respect to the orifice. In another aspect, the spool or sliding tube can circumscribe the inner tube (as opposed to the inner tube circumscribing the spool or sliding tube).

The inner tube 122 can be rigidly affixed to the housing 100, and can extend out of the housing and into the bore 76 of the upper cap 72 or manifold, through the proximal portion 66a of the channel 66 and to the distal portion 66b of the channel. In addition, the inner tube 122 can define an inner flow channel. The housing 100 (or the fitting 104 thereof) can form or can include an outer tube 126 circumscribing the inner tube 122 and spaced apart therefrom, and defining an outer annular flow channel circumscribing the inner flow channel. The inner and outer tubes 122 and 126 are coupled to the hydraulic flow channel 66 in the upper cap 72 or manifold. The outer tube 126 extends into the bore 76 of the upper cap 72 or manifold and to the proximal portion 66a of the channel 66. Thus, the orifice(s) 110, and the opening(s) 118, are disposed between the inner and outer flow channels. The inner tube 122 and the outer tube 126 each have a distal end with the one extending beyond the other, namely the inner tube can extend beyond the outer tube. Thus, the inner tube 122 can extend through the bore 76 to the distal portion 66b of the flow channel 66, while the outer tube 126 can extend into the bore 76 and to the proximal portion 66a of the flow channel 66.

As stated above, the electric actuator 90 is coupled to the hydraulic valve 80 to move the orifice(s) 110 and the spool 114 or sliding tube 116 with respect to one another. The actuator 90 includes a permanent magnet 140 and a coil 144 (removed for clarity) movable with respect to one another. The magnet 140 can have an outer wall or cup with an annular shape or a cup shape with an inner post forming an annular space between the outer wall and the inner post. The magnet 140 has or creates a magnetic field. The coil 144 can have an annular wall or cup sized to fit in the annular space of the magnet. The coil 144 can include wires wrapped or coiled around the wall or cup. Thus, the coil 144 can be movably positioned in the magnetic field of the magnet 140. A current can be applied to the coil 144 to move the coil with respect to the magnet 140. As described above, the current applied to the coil 144 in the magnetic field of the magnet 140 produces a force that is directly proportional to the electric current applied. In addition, the coil 144, and thus the control valve 60, has a substantially linear time and force response. Furthermore, the coil 144, and thus the spool 114 or sliding tube 116, is bi-directionally driven by the current, or polarity thereof. The electric current applied to the coil 144 causes the coil, and thus the spool 114 or sliding tube 116, to move in either a first direction or a second direction based on a polarity of the electric current. Thus, the coil 144, spool 144 and sliding tube 166 are reciprocally positionable with current polarity induced, bi-directional movement, by selectively changing the polarity of the electric current applied to the electric actuator 90 or coil 144 thereof. Thus, the spool 114 and sliding tube 116 can be selectively positioned and bi-directionally driven in back and forth directions, so that the hydraulic valve 80 selectively varies the resistance, or effective surface area or size of the opening between the orifice(s) 110 and opening(s) 118, of the hydraulic valve 80, via the position of the spool 114 or sliding tube 166 with respect to the inner tube 122, to the flow of hydraulic fluid through the flow channel or orifice(s) 110 and opening(s) 118 thereof. The control valve 60 or actuator 90 can have a rapid response rate, greater than 100 cycles per second, and a low power consumption, less than 1.8 Watts (i.e. or 150 mA @ 12V). Furthermore, the control valve 60, and the coil 144 thereof, can be selectively and proportionally positionable, proportional to an amount of the electric current applied to coil or the control valve. Thus, a selective and variable amount of electric current with variable polarity applied to the coil or control valve selectively and proportionally varies the resistance of the control valve, or the hydraulic valve 80 thereof, to the flow of hydraulic fluid through the flow channel. While the coil has been described above as movable with respect to a permanent magnet, it is contemplated that such a configuration can be reversed, with the magnet coupled to the spool or sliding tube, and movable with respect to the coil.

The control valve 60 can be characterized as a voice coil valve, and the actuator 90 can be characterized as a voice coil. Therefore, the prosthetic knee 10 and hydraulic system 40 thereof can utilize a voice coil valve. As noted above, the control valve 60 or voice coil valve described above provides bi-directional positioning, proportional control, rapid response and/or low power consumption. The use of the control valve 60 or voice coil valve described above allows the coil, spool and sliding tube to be driven in either direction without requiring a spring for return motion, which in turn reduces the power consumption of the control valve, which can result in longer operational periods between charging and/or smaller power supplies (e.g. batteries), resulting in greater freedom and less weight for the amputee. In addition, the use of the control valve 60 or voice coil valve described above allows the hydraulic system 40 and prosthetic knee 10 to have a faster response time to provide a more natural gait to the amputee and/or to provide a more natural transition between sitting and standing, and/or climbing stairs.

The control valve 60 or voice coil valve can be carried by and attached to the cylinder 54 or another frame member of the hydraulic actuator or damper 50. As described above, the housing or cartridge 100 of the control valve 60 or voice coil valve can have a fitting 104 and/or an outer tube 126 that engages and attaches to the housing, and thus the control valve, to the upper cap 72 of the cylinder. In addition, the control valve 60 or voice coil valve, or housing 100 thereof, can be located behind the cylinder 54. Furthermore, the control valve 60 or voice coil valve can be oriented with a path of travel of the coil 144, spool 114 and sliding tube 116 parallel with a path of travel of the piston 58. The position and orientation of the control valve 60 or voice coil valve can create a more compact and smaller profile for the prosthetic knee, and thus greater freedom, comfort and natural movement for the amputee, because the control valve 60 or voice coil valve can be larger than prior art solenoid valves.

Figures 5B, 6B:
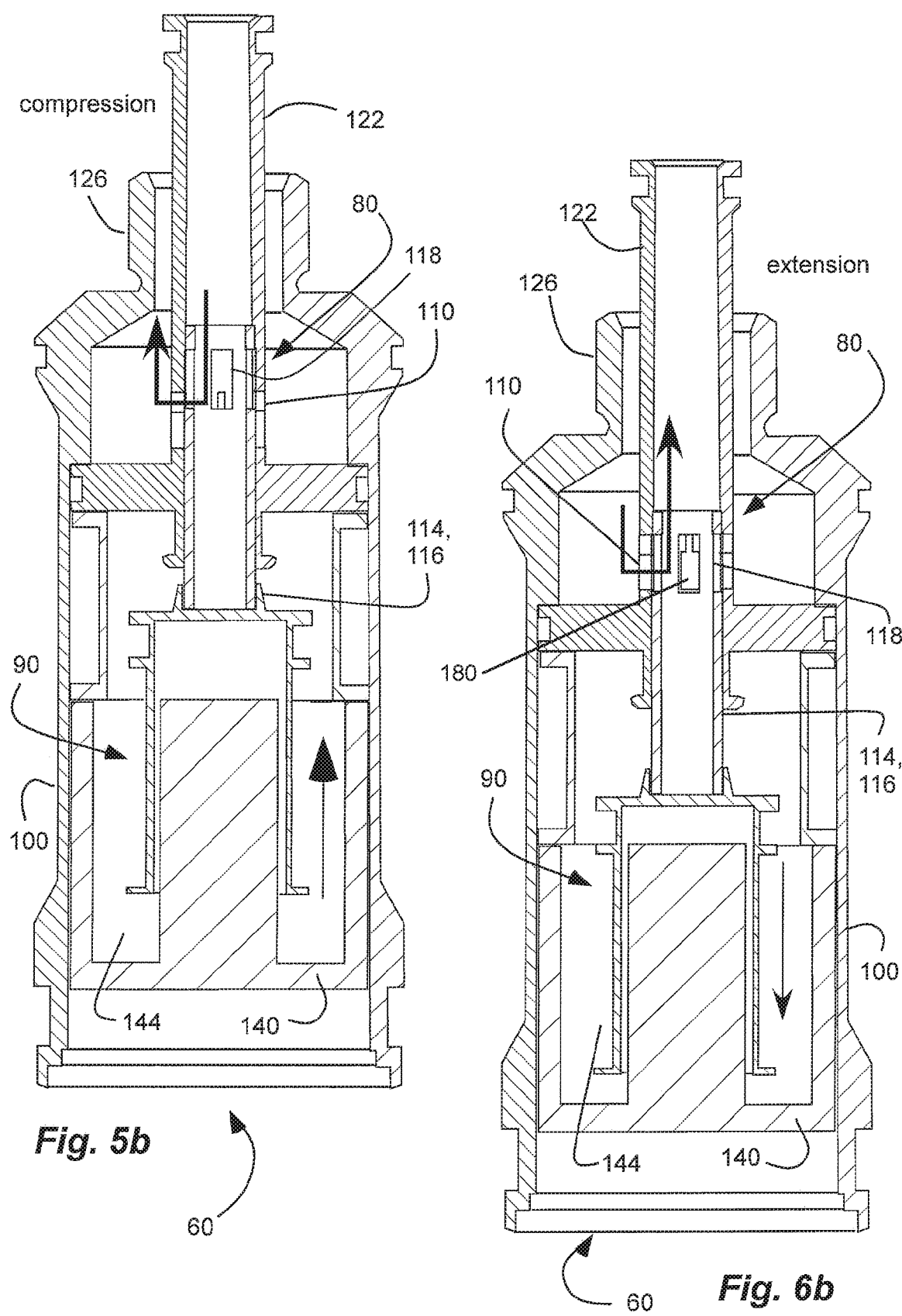
FIG. 5b is a cross-sectional schematic view of a control valve or voice coil valve of FIG. 1 shown in cylinder compression or knee flexion.
FIG. 6b is a cross-sectional schematic view of the control valve or voice coil valve of FIG. 1 shown in extension.

In addition, the control valve 60 or voice coil valve, and thus the hydraulic valve 80, has a pair of different regions of substantially linear control. A first region provides a region of control during slow extension and/or retraction (or compression) of the hydraulic actuator or damper, between 1.5 to 2.5 inches per second and is by definition the smaller of the two regions; and a second region provides for a region of control during fast extension and/or retraction (or compression) of the hydraulic actuator or damper, between 6 to 8 inches per second. As described above, one or more orifices 110 in the inner tube 122 can be selectively aligned with one or more openings 118 of the sliding tube 116 to achieve the pair of control regions with different flow rates. In one aspect, the orifice(s) 110 can have a longitudinally varying width with a discrete change in width from a proximal end to a distal end along a longitudinal length of the orifice. For example, the orifice can have a larger or wider proximal end, and a smaller or narrower distal end, as shown in FIGS. 5b and 6b. Thus, the orifice 110 can have two discrete widths formed by two orifices sharing a common boundary that is open between the two orifices. As shown in FIGS. 5b and 6b, the orifice(s) 110 can have a larger proximal rectilinear (square or rectangular) shape and a smaller distal rectilinear shape, which share a common boundary and that are open to one another. In another aspect, a larger number of orifices(s) and opening(s) can be aligned or misaligned. In another aspect, the shape, size, number and/or location of the orifice(s) and/or opening(s) can be configured to provide the two linear regions.

Referring to FIGS. 5a-6b, the operation of the hydraulic system 40, the hydraulic actuator or damper 50, the control valve 60 or voice coil valve, the hydraulic valve 80 and electric actuator 90 is demonstrated. FIGS. 5a and b show the hydraulic system in compression and the control valve more "closed" or more restricted to have a lower flow rate and a greater resistance, which can correspond to knee flexion (or the lower member 18 pivoting towards the upper member 14). Thus, the knee can flex or compress more slowly or with greater resistance. It is noted, however, that the knee can flex or compress more rapidly and with lesser resistance (i.e. with the control valve more "open" or less restricted) depending on the gait cycle. FIGS. 6a and b show the hydraulic system in extension and the control valve more "open" or less restricted to have a greater flow rate and a lesser resistance, which can correspond to knee extension (or the lower member 18 pivoting away the upper member 14). Thus, the knee can extend more rapidly or with lesser resistance. It is noted, however, that the knee can extend more slowly and with greater resistance (i.e. with the control valve more "closed" or more restricted) depending on the gait cycle.

Referring to FIGS. 5a and b, the hydraulic actuator or damper 50 is compressed; the piston 58 is compressed into the cylinder 54; hydraulic fluid is displaced by the piston out of the (lower) chamber or portion of the cylinder, through a portion of the channel in the lower cap 70, through the tube 74 to the upper cap 72 or manifold, and into the distal portion 66b of the channel 66 in the upper cap 72 or manifold. The hydraulic fluid is displaced into the control valve 60 or voice coil valve through and into the inner tube 122, and through and into the sliding tube 116 or spool 114, and to the opening(s) 118 in the sliding tube or spool. As shown in FIGS. 5a and b, the opening(s) 118 of the sliding tube 116 or spool 114 is misaligned with the orifice(s) 110 in the inner tube 122, or aligned with the smaller or narrower distal end or portion thereof; creating a smaller cross-sectional area through which the fluid can flow, and thus increasing resistance to the flow and decreasing the flow rate so that the piston 58 moves with greater difficulty and more slowly in the cylinder 54, and the lower member 18 moves with greater difficulty and more slowly in compression. The hydraulic fluid is displaced through the opening(s) 118 of the sliding tube 116 or spool 114, and the orifice(s) 110 in the inner tube 122. The hydraulic fluid is displaced through the outer tube 126, out of the control valve 60 or voice coil valve, into the proximal portion 66a of the channel 66 in the upper cap 72 or manifold, and into the (upper) chamber or portion of the cylinder. (Because of the piston rod 62 in the upper chamber of the cylinder, the opposite sides of the chamber change volume unequally. Thus, excess fluid can be diverted into an overflow reservoir 154.) Also as shown in FIGS. 5a and b, the control valve 60 or voice coil valve, or actuator 90, has been moved in a first or distal direction under an applied current (and polarity) to selectively position the spool 114 or sliding tube 116, and thus selectively position or misalign the orifice(s) 110 and opening(s) 118. As discussed above, the control valve can be operated to move in a proximal direction to align the orifice(s) and the opening(s) to create a larger cross-sectional area, and thus reduce resistance to flow and increase the flow rate so that the lower member moves faster in extension, or when the knee is coming forward during the gait cycle.

Referring to FIGS. 6a and b, the hydraulic actuator or damper 50 is extended; the piston 58 is extended or withdrawn away from the cylinder 54; hydraulic fluid is displaced by the piston out of the (upper) chamber or portion of the cylinder, through a portion of the channel in the upper cap 72, and into a proximal portion 66a of the channel 66 in the upper cap 72 or manifold. The hydraulic fluid is displaced into the control valve 60 or voice coil valve through and into the outer tube 126, and to the orifice(s) 110 in the inner tube 122. As shown in FIGS. 6a and b, the opening(s) 118 of the sliding tube 116 or spool 114 is aligned with the orifice(s) 110 in the inner tube 122, or the larger or wider proximal end or portion thereof (or in this case the entire orifice); creating a larger cross-sectional area through which the fluid can flow, and thus reducing resistance to the flow and increasing the flow rate so that the piston 58 moves easier and more quickly in the cylinder 54, and the lower member moves easier and more quickly in extension. The hydraulic fluid is displaced through the opening(s) 118 of the sliding tube 116 or spool 114, and the orifice(s) 110 in the inner tube 122. The hydraulic fluid is displaced out of the control valve 60 or voice coil valve through and out of the sliding tube 116 or spool 114, and through and out of the inner tube 122 to the distal portion 66b of the channel 66 in the upper cap 72 or manifold. The hydraulic fluid is displaced through the tube 74 to the lower cap 70, and into the (lower) chamber or portion of the cylinder. (Again, because of the piston rod 62 in the upper chamber of the cylinder, the opposite sides of the chamber change volume unequally. Thus, the deficient fluid can be withdrawn from the overflow reservoir.) Also as shown in FIGS. 6a and b, the control valve 60 or voice control valve, or actuator 90, has been moved in a second or proximal direction under an applied current (and opposite polarity) to selectively position the spool 114 or sliding tube 116, and thus selectively position or align (or misalign) the orifice(s) 110 and opening(s) 118. As discussed above, the control valve can be operated to move in a distal direction to misalign the orifice(s) and the opening(s) to create a smaller cross-sectional area, and thus increase resistance to flow and reduce the flow rate so that the lower member moves slower in compression, or knee flexion.

Thus, as described above, the control valve or voice coil valve provides selectively adjustable greater resistance and less flow rate to compression. In another aspect, the operation as described above can be reversed, with the control valve or voice coil valve providing greater resistance and less flow rate to extension.

In another aspect, an opposite rod can be formed on the piston on the opposite side of the piston rod so that the opposite chambers change volume equally. For example, see FIGS. 22 and 23.

As stated above, the prosthetic knee 10 can include a power supply (such as batteries 158) and control electronics (such as a circuit board with a microprocessor, not shown and as understood by those of skill in the art). The actuator 90 can be electrically coupled to the control electronics and power supply to control and drive the actuator, and thus the operation of the prosthetic knee. In addition, the prosthetic knee can have pressure sensors 162 operatively coupled to the flow channel 66 on opposite sides of the orifice(s) to sense pressure on opposite sides of the piston. The sensors can be attached to the upper cap 72 or manifold, and operatively coupled to the proximal and distal portions 66a and 66b of the flow channel. The sensors can be electrically coupled to the control electronics.

The prosthetic device 10 and/or the control valve 60 or voice coil valve can also have a non-powered state in case power is lost, with a pressure control valve that is opened by a pressure imbalance, thus allowing hydraulic fluid flow between the opposite sides of the chamber. The flow control valve can allow different flow rates and different resistance in opposite directions through a separate set of the hydraulic flow channels in the non-powered state. The pressure control valve can allow a higher flow rate and a lower resistance during extension of the hydraulic actuator or damper, or the pair of prosthetic members. In addition, the pressure control valve can allow a lower flow rate and a higher resistance during retraction of the hydraulic actuator or damper, or the pair of prosthetic members. The pressure control valve can include at least one safety port 180 through a spool, such as the spool of the control valve. The coil can have an unpowered positioned, either biased or unbiased, in which the safety port of the spool or sliding tube is aligned with the orifice or other safety port in the inner tube. The operation as described above can be reversed.

Figure 7:
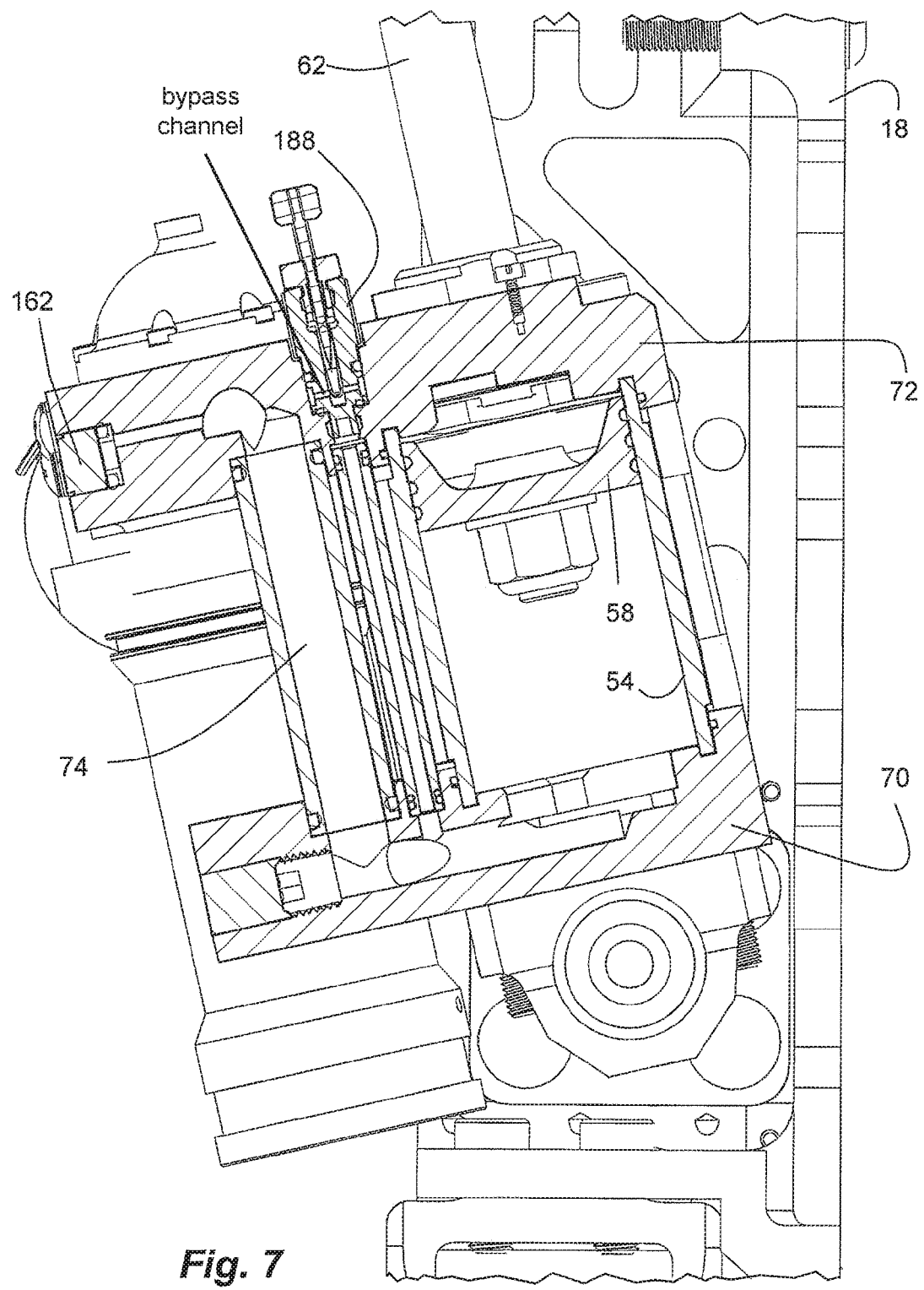
FIG. 7 is a partial cross-sectional side view of the prosthetic knee of FIG. 1, taken along line 3-3 in FIG. 1.
Figure 11:
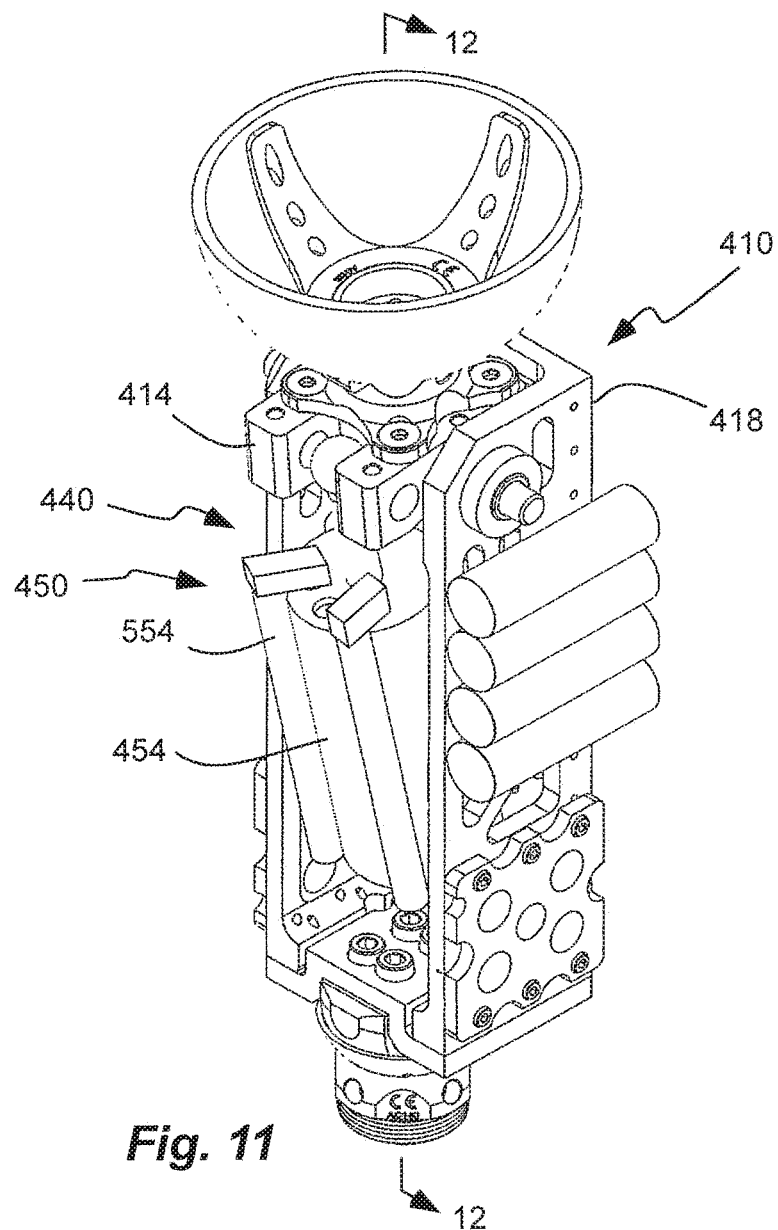
FIG. 11 is a perspective view of another prosthetic knee in accordance with another embodiment of the present invention.
Figure 12:
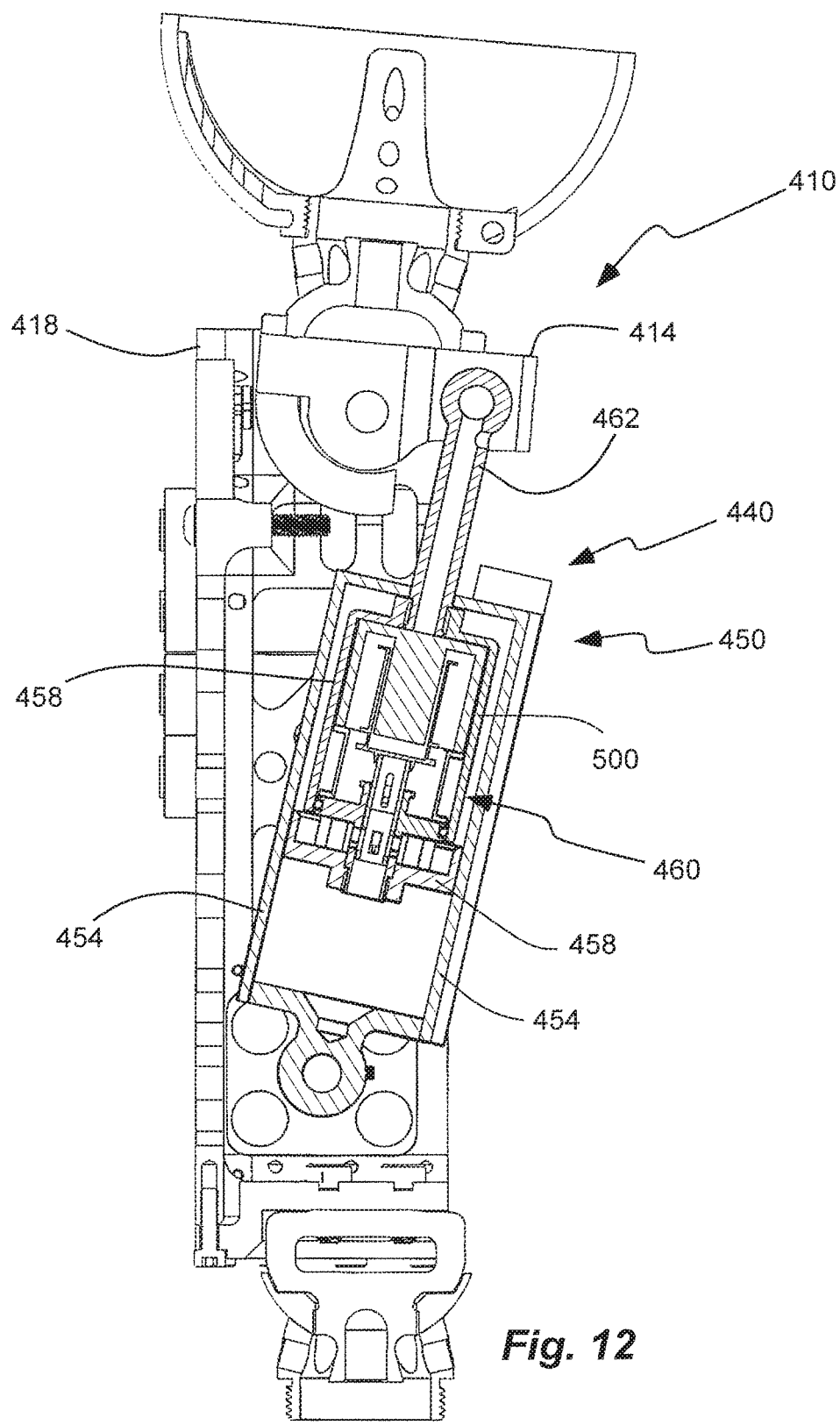
FIG. 12 is a cross-sectional side view of the prosthetic knee of FIG. 11, taken along line 12-12 in FIG. 11.

Furthermore, as shown in FIG. 7, the prosthetic knee 10, or hydraulic system thereof, can have an externally adjustable bypass valve 188 that is manually operated and fluidly coupled to a bypass channel between the opposite sides of the cylinder to allow the members to pivot.

Referring to FIGS. 8-10, another prosthetic knee 310 is shown in accordance with an embodiment of the present invention, which is similar in most respects to that described above, and which description is hereby incorporated herein by reference. As discussed above, the coupling of the hydraulic actuator or damper 350 can be reversed with respect to that described above, with the cylinder 354 coupled to the upper member 314, and the piston rod 362 of the piston 358 coupled to the lower member 318. In addition, the control valve 360 or voice coil valve can be carried by and directly coupled to the hydraulic actuator or damper 350. The control valve can have a housing that is integrally formed from at the same time with the cylinder (and even the cap opposite the piston) as a single monolithic housing to reduce the overall size of the hydraulic system 340 and accommodate the larger size of the voice coil valve (with respect to a solenoid valve). Thus, the control valve 360 or voice coil valve can be carried by and attached to the cylinder 354 or another frame member of the hydraulic actuator or damper 350. Furthermore, the control valve (or path of travel of the spool) can be aligned with the hydraulic actuator or damper (or the path of travel of the piston); which can help reduce the size or profile of the hydraulic system.

Referring to FIGS. 11-14c, another prosthetic knee 410 is shown in accordance with an embodiment of the present invention, which is similar in most respects to that described above, and which description is hereby incorporated herein by reference, but with a control valve or voice coil valve disposed in the piston. As discussed above, the coupling of the hydraulic actuator or damper 450 can be reversed with respect to that described above in FIGS. 1-7, with the cylinder 454 coupled to the upper member 414, and the piston rod 462 of the piston 458 coupled to the lower member 418.

In addition, the control valve 460 or voice coil valve can be carried by and disposed in the piston 458. The control valve 460 or voice coil valve is movable with the piston 458 inside the hydraulic cylinder 454 or chamber, and the hydraulic channel 466 extends through the piston 458.

The control valve 460 or voice coil valve, and the hydraulic valve 480 and the actuator 490 thereof, can be disposed in a housing or cartridge 500 attached to the piston 458. The hydraulic channel 466 can be formed by a central opening in a face of the piston on one side, and an annular opening on the other side of the piston between the housing and the piston.

The hydraulic valve 480 of the control valve 460 is operatively coupled in the hydraulic flow path or channel 466, and includes at least one orifice 110 and a spool 114 movable with respect to one another to selectively resist flow of the hydraulic fluid through the orifice. The spool 114 can be selectively positioned with respect to the orifice(s) 110 to selectively increase and decrease a cross-sectional area through which the hydraulic fluid can flow. The spool 114 can be sliding tube 116 defining, and can have a distal end or at least one distal opening 118 that is selectively positionable with respect to the orifice 110. The distal opening 118 can be formed in a sidewall of the sliding tube 116, or the open end thereof. The orifice(s) 110 can be formed in an inner tube 122 circumscribing the sliding tube 116 or spool 114. Thus, the spool 114 or sliding tube 116 can be selectively positioned by the actuator to selectively position the orifice(s) 110 and opening(s) 118 with respect to one another, and selectively increase and decrease a cross-sectional area through which the hydraulic fluid can flow. In another aspect, a distal end of the sliding tube or spool can be positioned with respect to the orifice. The sliding tube 116 can slide within the inner tube 122. In another aspect, the spool or sliding tube can circumscribe the inner tube (as opposed to the inner tube circumscribing the spool or sliding tube). The inner tube 122 can be rigidly affixed to the housing 500, and can extend out of the housing and into the piston 458, and through the piston to the opposite side thereof.

As stated above, the electric actuator 490 is coupled to the hydraulic valve 480 to move the orifice(s) 110 and the spool 114 or sliding tube 116 with respect to one another. The actuator 490 includes a permanent magnet 140 and a coil 144 movable with respect to one another, and disposed in the housing 500 movable with the piston 458 in the cylinder 454. The magnet 140 can have an outer wall or cup with an annular shape or a cup shape with an inner post forming an annular space between the outer wall and the inner post. The magnet 140 has or creates a magnetic field. The coil 144 can have an annular wall or cup sized to fit in the annular space of the magnet. The coil 144 can include wires wrapped or coiled around the wall or cup. Thus, the coil 144 can be movably positioned in the magnetic field of the magnet 140. A current can be applied to the coil 144 to move the coil with respect to the magnet 140. As described above, the current applied to the coil 144 in the magnetic field of the magnet 140 produces a force that is directly proportional to the electric current applied. In addition, the coil 144, and thus the control valve 60, has a substantially linear time and force response. Furthermore, the coil 144, and thus the spool 114 or sliding tube 116, is bi-directionally driven by the current, or polarity thereof. The electric current applied to the coil 144 causes the coil, and thus the spool 114 or sliding tube 116, to move in either a first direction or a second direction based on a polarity of the electric current. Thus, the coil 144, spool 144 and sliding tube 116 are reciprocally positionable with current polarity induced, bi-directional movement, by selectively changing the polarity of the electric current applied to the electric actuator 90 or coil. Thus, the spool 114 and sliding tube 116 can be selectively positioned and bi-directionally driven in back and forth directions, so that the hydraulic valve 80 selectively varies the resistance, or effective surface area or size of the opening between the orifice(s) 110 and opening(s) 118, of the hydraulic valve 80, via the position of the spool 114 or sliding tube 116 with respect to the inner tube 122, to the flow of hydraulic fluid through the flow channel or orifice(s) 110 and opening(s) 118 thereof. The control valve 60 or actuator 90 can have a rapid response rate, greater than 100 cycles per second, and a low power consumption, less than 1.8 Watts (i.e. or 150 mAmps @ 12V). Furthermore, the control valve 60, and the coil 144 thereof, can be selectively and proportionally positionable, proportional to an amount of the electric current applied to coil or the control valve. Thus, a selective and variable amount of electric current applied to the coil or control valve selectively and proportionally varies the resistance of the control valve, or the hydraulic valve 80 thereof, to the flow of hydraulic fluid through the flow channel.

The control valve 460 can be characterized as a voice coil valve, and the actuator 490 can be characterized as a voice coil. Therefore, the prosthetic knee 410 and the hydraulic system 440 and the piston 458 thereof can utilize a voice coil valve. As noted above, the control valve 460 or voice coil valve described above provides bi-directional positioning, proportional control, rapid response and/or low power consumption. The use of the control valve 460 or voice coil valve described above allows the coil, spool and sliding tube to be driven in either direction without requiring a spring for return motion, which in turn reduces the power consumption of the control valve, which can result in longer operational periods between charging and/or smaller power supplies (e.g. batteries), resulting in greater freedom and less weight for the amputee. In addition, the use of the control valve 460 or voice coil valve described above allows the hydraulic system 440 and prosthetic knee 410 to have a faster response time to provide a more natural gait to the amputee and/or to provide a more natural transition between sitting and standing, and/or climbing stairs. Disposing the control valve 460 or voice coil valve in the piston 458 also allows for a more compact size or profile, but at the expense of cylinder height or length.

While the above control valve 460 or voice coil valve has been described as having a coil movable with respect to a permanent magnet, it is contemplated that such a configuration can be reversed, with the magnet coupled to the spool or sliding tube, and movable with respect to the coil.

The control valve 460 or voice coil valve can also have a non-powered state in which case power is lost, and the control valve is opened by a pressure imbalance, thus allowing hydraulic fluid flow between the opposite sides of the chamber. The control valve can allow different flow rates and different resistance in opposite directions through the hydraulic flow channel in the non-powered state. The control valve can allow a higher flow rate and a lower resistance during extension of the hydraulic actuator or damper, or the pair of prosthetic members. In addition, the control valve can allow a lower flow rate and a higher resistance during retraction the hydraulic actuator or damper, or the pair of prosthetic members. The control valve can include at least one safety port 580 through a spool of the control valve. The coil can have an unpowered positioned, either biased or unbiased, in which the safety port of the spool or sliding tube is aligned with the orifice or other safety port in the inner tube.

In addition, the control valve 460 or voice coil valve, and thus the hydraulic valve 480, has a pair of different, substantially linear control regions, as described above.

Figure 13B:
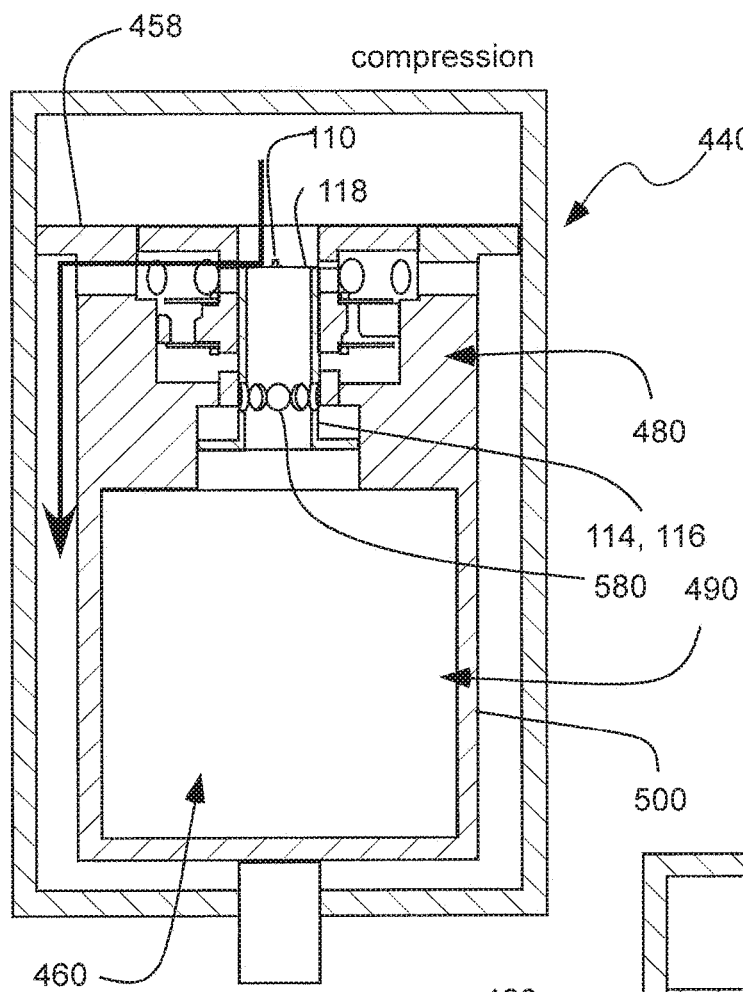
FIG. 13b is a schematic cross-sectional side view of a control valve or voice coil valve of FIG. 11, shown in cylinder compression or knee flexion.

Referring to FIGS. 13a-14c, the operation of the hydraulic system 440, the hydraulic actuator or damper 450, the control valve 460 or voice coil valve, the hydraulic valve 480 and electric actuator 490 is demonstrated with the valve disposed within the piston. FIGS. 13a and b show the hydraulic system in compression and the control valve more "closed" or more restricted to have a lower flow rate and a greater resistance, which can correspond to knee flexion (or the lower member 418 pivoting towards the upper member 414). Thus, the knee can flex or compress more slowly or with greater resistance. It is noted, however, that the knee can flex or compress more rapidly and with lesser resistance (i.e. with the control valve more "open" or less restricted) depending on the gait cycle. FIGS. 14a and b show the hydraulic system in extension and the control valve more "open" or less restricted to have a greater flow rate and a lesser resistance, which can correspond to knee extension (or the lower member 418 pivoting away the upper member 414). Thus, the knee can extend more rapidly or with lesser resistance. It is noted, however, that the knee can extend more slowly and with greater resistance (i.e. with the control valve more "closed" or more restricted) depending on the gait cycle.

Referring to FIGS. 13a and b, the hydraulic actuator or damper 450 is compressed; the piston 458 is compressed into the cylinder 454; hydraulic fluid is displaced by the piston out of the (lower) chamber or portion of the cylinder (note that the control valve is inverted in FIG. 13a), through the central opening in the piston and into the inner tube 122. The hydraulic fluid is displaced into the control valve 460 or voice coil valve through and into the inner tube 122, and through and into the sliding tube 116 or spool 114, and to the opening(s) 118 in the sliding tube or spool. As shown in FIGS. 13a and b, the opening(s) 118 of the sliding tube 116 or spool 114 is misaligned with the orifice(s) 110 in the inner tube 122, or aligned with the smaller or narrower distal end or portion thereof; creating a smaller cross-sectional area through which the fluid can flow, and thus increasing resistance to the flow and decreasing the flow rate so that the piston moves under greater resistance and more slowly in the cylinder, and the lower member moves with difficulty and more slowly in flexion. The hydraulic fluid is displaced through the opening(s) 118 of the sliding tube 116 or spool 114, and the orifice(s) 110 in the inner tube 122. The hydraulic fluid is displaced through the channel 466 in the piston, and into the (upper) chamber or portion of the cylinder (again, note the control valve is inverted). (Because of the piston rod 462 in the upper chamber of the cylinder, the opposite sides of the chamber change volume unequally. Thus, excess fluid can be diverted into an overflow reservoir 554. In another aspect, an opposite rod can be formed on the piston on the opposite side of the piston rod so that the opposite chambers change volume equally.) Also as shown in FIGS. 13a and b, the control valve 460 or voice coil valve, or actuator 490, has been moved in a first or distal direction under an applied current (and polarity) to selectively position the spool or sliding tube, and thus selectively position or align the orifice(s) and opening(s).

Figure 14B:
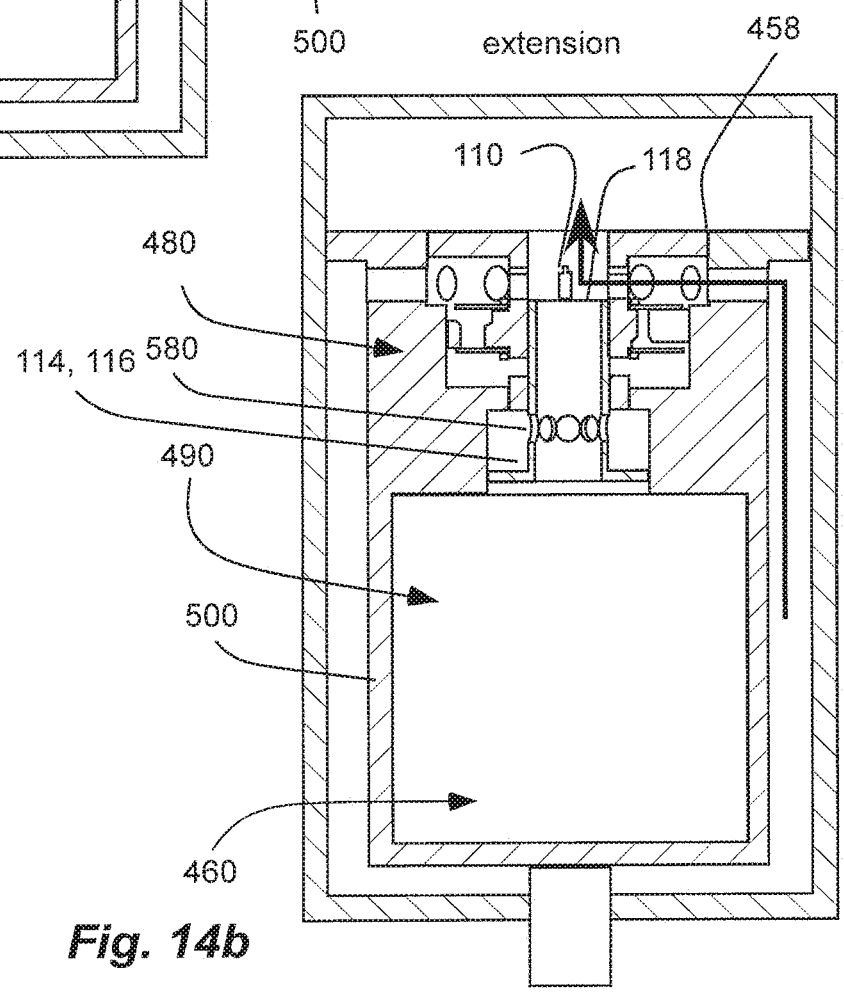
FIG. 14b is a schematic cross-sectional side view of the control valve or voice coil valve of FIG. 11, shown in cylinder extension and knee extension.
Figure 17:
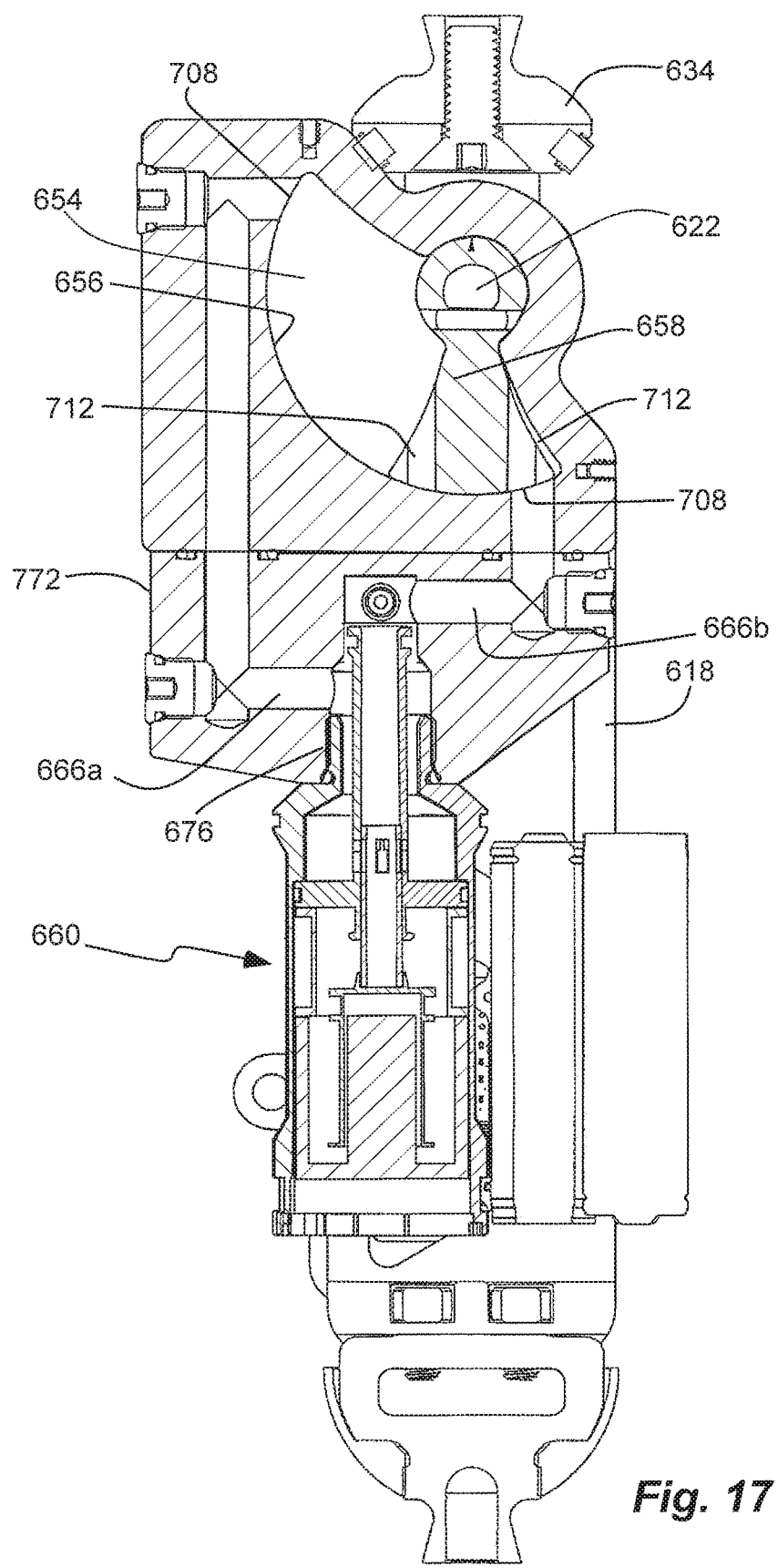
FIG. 17 is a cross-sectional side view of the prosthetic knee of FIG. 15, taken along line 17-17 in FIG. 15.
Figure 18:
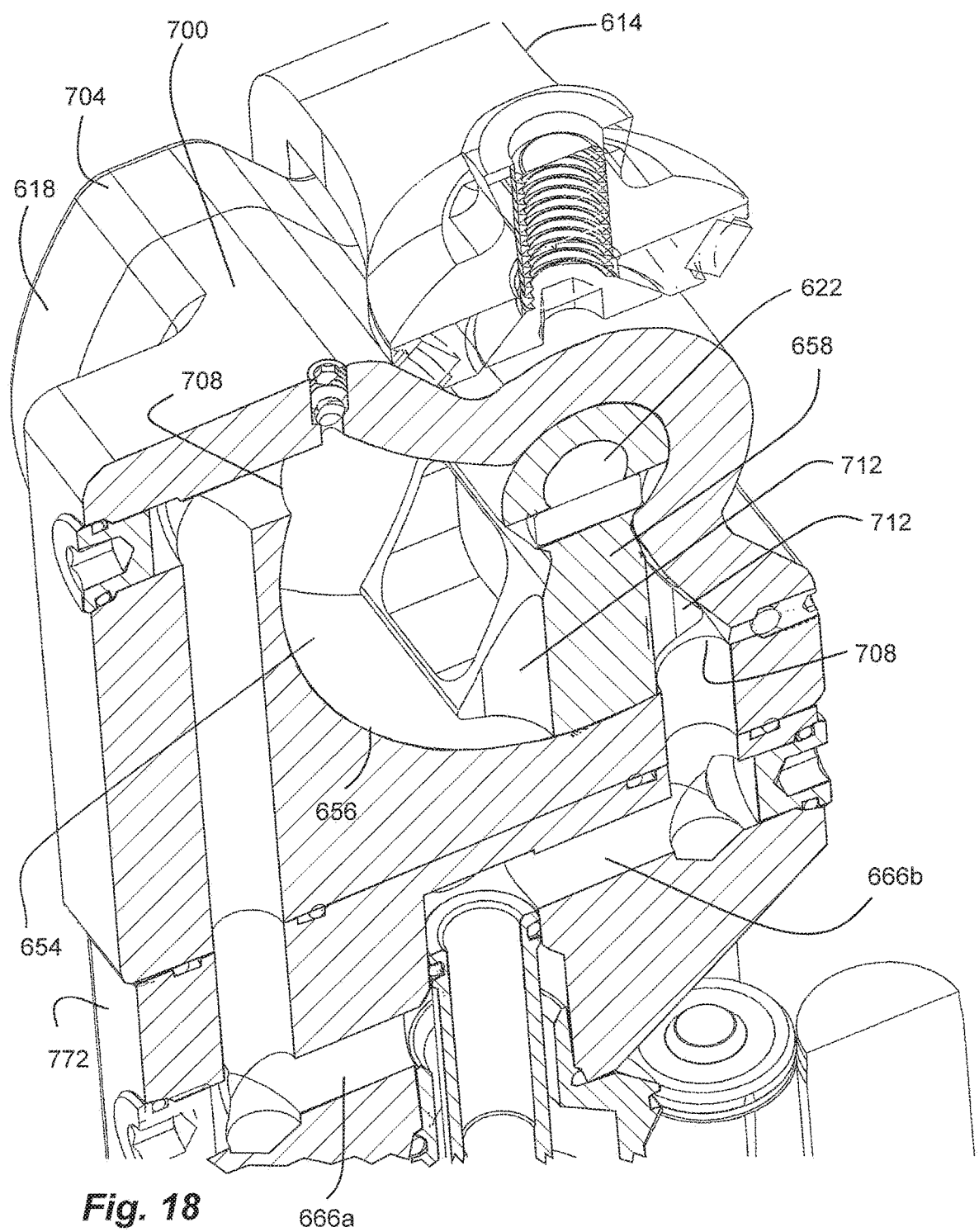
FIG. 18 is a partial cross-sectional perspective view of the prosthetic knee of FIG. 15.
Figure 19:
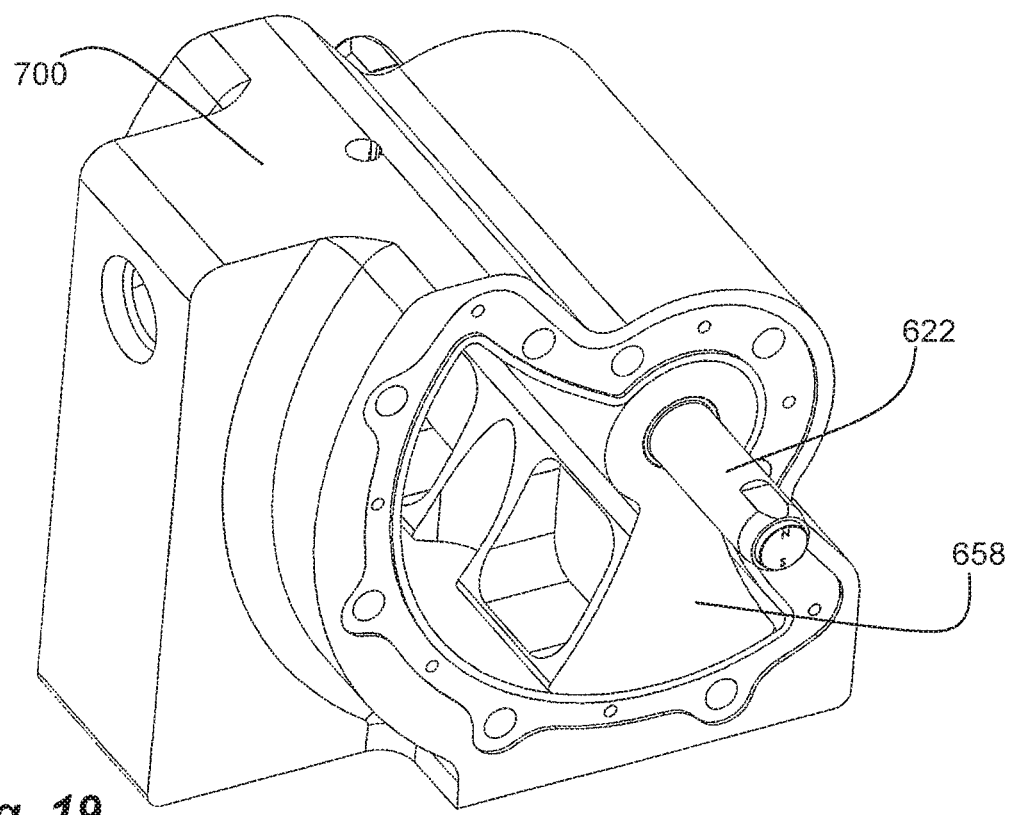
FIG. 19 is partial perspective view of a portion of a rotary vane type hydraulic actuator or damper of the prosthetic knee of FIG. 15, and namely a central block forming a portion of a hydraulic chamber with a rotary vane therein.

Referring to FIGS. 14a and b, the hydraulic actuator or damper 450 is extended; the piston 458 is extended or withdrawn away from the cylinder 454; hydraulic fluid is displaced by the piston out of the (upper) chamber or portion of the cylinder (again, note that the control valve is inverted), and through the channel 466 in the piston. The hydraulic fluid is displaced into the control valve 460 or voice coil valve through the annular opening, and to the orifice(s) 110 in the inner tube 122. As shown in FIGS. 14a and b, the opening(s) 118 of the sliding tube 116 or spool 114 is aligned with the orifice(s) 110 in the inner tube 122, or the larger or wider proximal end or portion thereof (or in this case the entire orifice); creating a larger cross-sectional area through which the fluid can flow, and thus reducing resistance to the flow and increasing the flow rate so that the piston moves easier and more quickly in the cylinder, and the lower member moves easier and more quickly in flexion. The hydraulic fluid is displaced through the opening(s) 118 of the sliding tube 116 or spool 114, and the orifice(s) 110 in the inner tube 122. The hydraulic fluid is displaced out of the control valve 460 or voice coil valve through and out of the sliding tube 116 or spool 114, through and out of the inner tube 122 to the central opening in the piston, and into the (lower) chamber or portion of the cylinder (again note that the control valve is inverted).

Again, because of the piston rod 462 in the upper chamber of the cylinder, the opposite sides of the chamber change volume unequally. Thus, the deficient fluid can be withdrawn from the overflow reservoir.

In another aspect, the piston rod can continue through the piston and exit the opposite side of the working chamber so that the sum of the volume in the opposite chambers doesn't change.

As described above, the linear piston damper system (or piston and cylinder) can utilize tightly toleranced components which eliminate the need for elastomeric seals to separate the sides of the hydraulic chamber. By using a "metal-on-metal" fit between the piston and cylinder, the seal drag (or stiction) which would be transferred to the amputee as a jarring or disjointed feeling, can be entirely removed from the system, or greatly reduced. The precision that can be required to form a hydraulic working chamber capable of locking without weeping can require a gap between the acting surfaces of the piston and cylinder on the order of 0.005 mm (0.0002 in) (i.e. between 0.05 mm and 0.0005 mm). Furthermore, the surface finish that can required to facilitate smooth actuation on both surfaces of the piston and cylinder can be between 0.20 to 0.41 µm (8 to 16 µin) Ra finish.

Also as shown in FIGS. 14a and b, the control valve 460 or voice coil control valve, or actuator 490, has been moved in a second or proximal direction under an applied current (and opposite polarity) to selectively position the spool or sliding tube, and thus selectively position or align (or misalign) the orifice(s) and opening(s).

The control valve 460 or voice coil valve can also have a non-powered state in which case power is lost, and the control valve is opened by a pressure imbalance, thus allowing hydraulic fluid flow between the opposite sides of the chamber. The control valve can allow different flow rates and different resistance in opposite directions through the hydraulic flow channel in the non-powered state. The control valve can allow a higher flow rate and a lower resistance during extension of the hydraulic actuator or damper, or the pair of prosthetic members. In one aspect, the control valve can have a check valve or plurality of check valves 566 with a larger bore oriented and configured to allow the higher flow rate and the lower resistance during extension, as shown in FIG. 14c. In addition, the check valve can allow a lower flow rate and a higher resistance during retraction the hydraulic actuator or damper, or the pair of prosthetic members. In one aspect, the control valve can have a check valve 568 with a smaller bore oriented and configured to allow the lower flow rate and the higher resistance during compression, as shown in FIG. 13c, with flexion being the opposite. The control valve can include at least one safety port 580 through a spool of the control valve. The coil can have an unpowered positioned, either biased or unbiased, in which the safety port of the spool or sliding tube is aligned with the orifice or other safety port in the inner tube.

As also shown in FIGS. 13a and 14a, the piston rod 462 can have a hollow 570 with electrical wires 574 electrically coupled to the coil in the piston and extending through the hollow of the piston rod to exit the hydraulic chamber.

While the above control valve 460 or voice coil valve has been described as being disposed in and carried by the piston, it is contemplated that such a configuration can be reversed, with the control valve or voice coil valve disposed in and carried by the cylinder.

Disposing the control valve or voice coil valve in the hydraulic actuator or damper, with the path of travel of the spool collinear or aligned with the path of travel of the piston, can lengthen the hydraulic actuator or damper, but also reduce the lateral size or profile of the hydraulic system to increase comfort and use to the amputee.

Referring to FIGS. 15-20, another prosthetic knee 610 is shown in accordance with an embodiment of the present invention, which is similar in most respects to that described above, and which description is hereby incorporated herein by reference, but with a rotary vane type hydraulic actuator or damper 650. The hydraulic system 640 and hydraulic actuator or damper 650 can be coupled between the upper and lower members 614 and 618 that are pivotally coupled together at a primary pivot, rotor or axle 622.

The hydraulic actuator or damper 650 includes a hydraulic chamber, namely a rotary chamber 654 forming an arc with an apex and an opposite outer arcuate concave wall 656 that is rigidly coupled to the lower member 618, and pivotally coupled to the upper member 614. The chamber 654 can be formed by or can include a central block 700 forming the hydraulic chamber with the arc formed therein and open on lateral sides, and a pair of plates 704 closing the open lateral sides of the central block. The plates 704 can form all or a portion of the lower member 618 or a shank link or a shin frame. Thus, the number of parts is reduced.

The hydraulic actuator or damper 660 also includes a piston or rotary vane 658 pivotally disposed in the rotary chamber 656, and rigidly coupled to the rotor 622 and the upper member 614. The rotor 622 extends through the rotary chamber 656 at the apex thereof, and is pivotal with respect to the rotary chamber. The rotary vane 658 has a proximal end attached to the rotor 622, and an opposite distal end with an outer arcuate convex wall matching the wall 656 of the rotary chamber. The vane 658 divides the chamber 656 into opposite sides.

Hydraulic fluid can fill the chamber, and can be displaced from one side of the chamber to the other as the vane moves therein. A hydraulic flow channel 666 is fluidly coupled between the opposite sides of the chamber to allow the hydraulic fluid to move or displace between the opposite sides of the chamber as the vane moves therein. The hydraulic flow channel 666 is coupled to both sides of the rotary chamber 654 at openings 708 in the outer arcuate concave wall 656 on opposite ends of the arc. The rotary vane, in this embodiment, 658 can have indentations 712 in opposite sides of the vane extending into the outer arcuate convex wall to accommodate the openings 708 of the hydraulic flow channel 608.

A manifold 772 can be attached to the central block 700. The manifold 772 can have at least a portion of the hydraulic flow channel 666 formed therein. Within the manifold 772, the hydraulic channel 666 can have a proximal portion 666a and a distal portion 666b (the proximal and distal positions being relative to the control valve 660. A bore 676 can be formed in the manifold 672, and can extend through the proximal portion 666a of the hydraulic channel 666 to the distal portion 666b. As described above, the control valve 660 or voice coil valve can be coupled to the manifold 772 at the bore 676. The control valve or voice coil valve can be disposed in the lower member 618 to create a smaller profile for user comfort.

Figure 20:
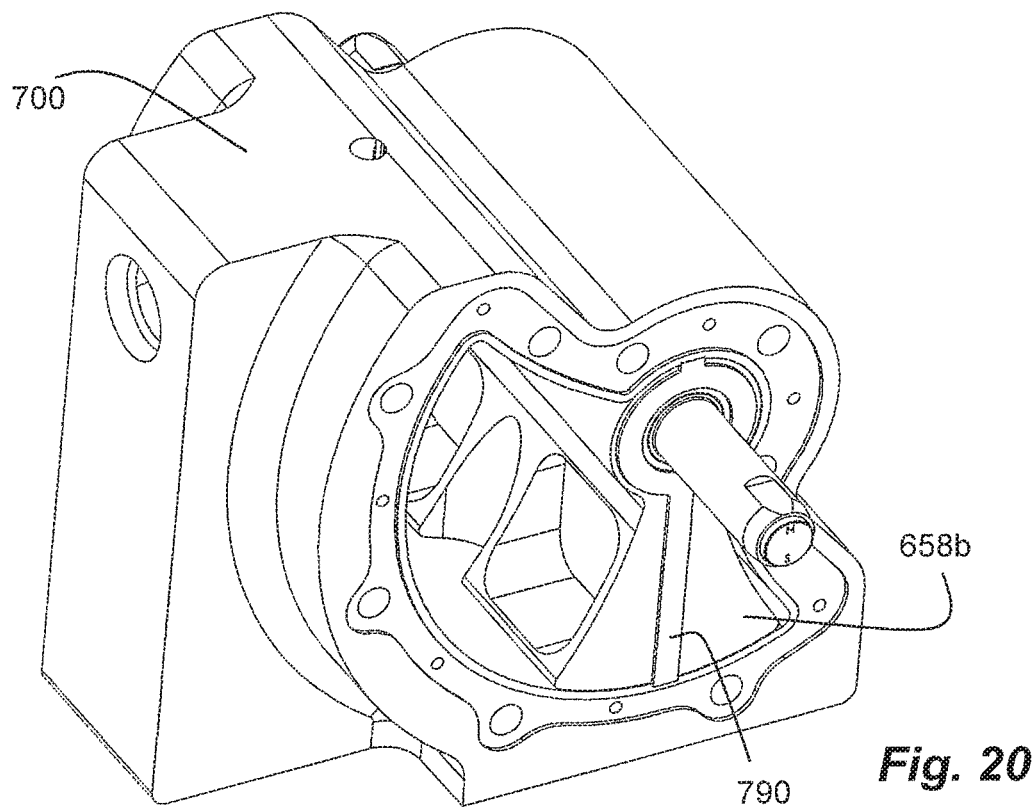
FIG. 20 is a partial perspective view of a portion of another rotary vane type hydraulic actuator or damper in accordance with another aspect of the present invention, and namely a central block forming a portion of a hydraulic chamber with a rotary vane therein.

The above central block 700 and rotary vane 658 can be made with close tolerance so that a seal is not necessary between the block and vane. The rotary vane damper system (or vane and rotary chamber) can utilize tightly toleranced components which eliminate the need for elastomeric seals to separate the sides of the hydraulic chamber. By using a "metal-on-metal" fit between the piston and cylinder, the seal drag (or stiction) which would be transferred to the amputee as a jarring or disjointed feeling, can be entirely removed from the system, or greatly reduced. The precision that can be required to form a hydraulic working chamber capable of locking without weeping can require a gap between the acting surfaces of the vane and rotary chamber on the order of 0.005 mm (0.0002 in). Furthermore, the surface finish that can required to facilitate smooth actuation on both surfaces of the vane and rotary chamber can be between 0.20 to 0.41 µm (8 to 16 µin) Ra finish. Referring to FIG. 20, another central block 700 and rotary vane 658b is shown with a seal 790 carried by the vane between the vane and the block.

One advantage of the prosthetic knee with the rotary vane configuration described above is that there are fewer working and/or moving parts, and thus lower cost and lower weight. In addition, there is no need for an overflow reservoir or variable volume section for the hydraulic fluid because the chamber has a fixed volume or the opposite sides of the chamber sum to a constant regardless of the angle of the vane. Torque is generated about the rotation axis by controlling the flow of fluid from one side of the vane to the other. Furthermore, a linear torque capability is independent of angle, i.e. there is no "fall-off" due to linkage ratio, as there would be with a linear piston damper system.

Figure 21:
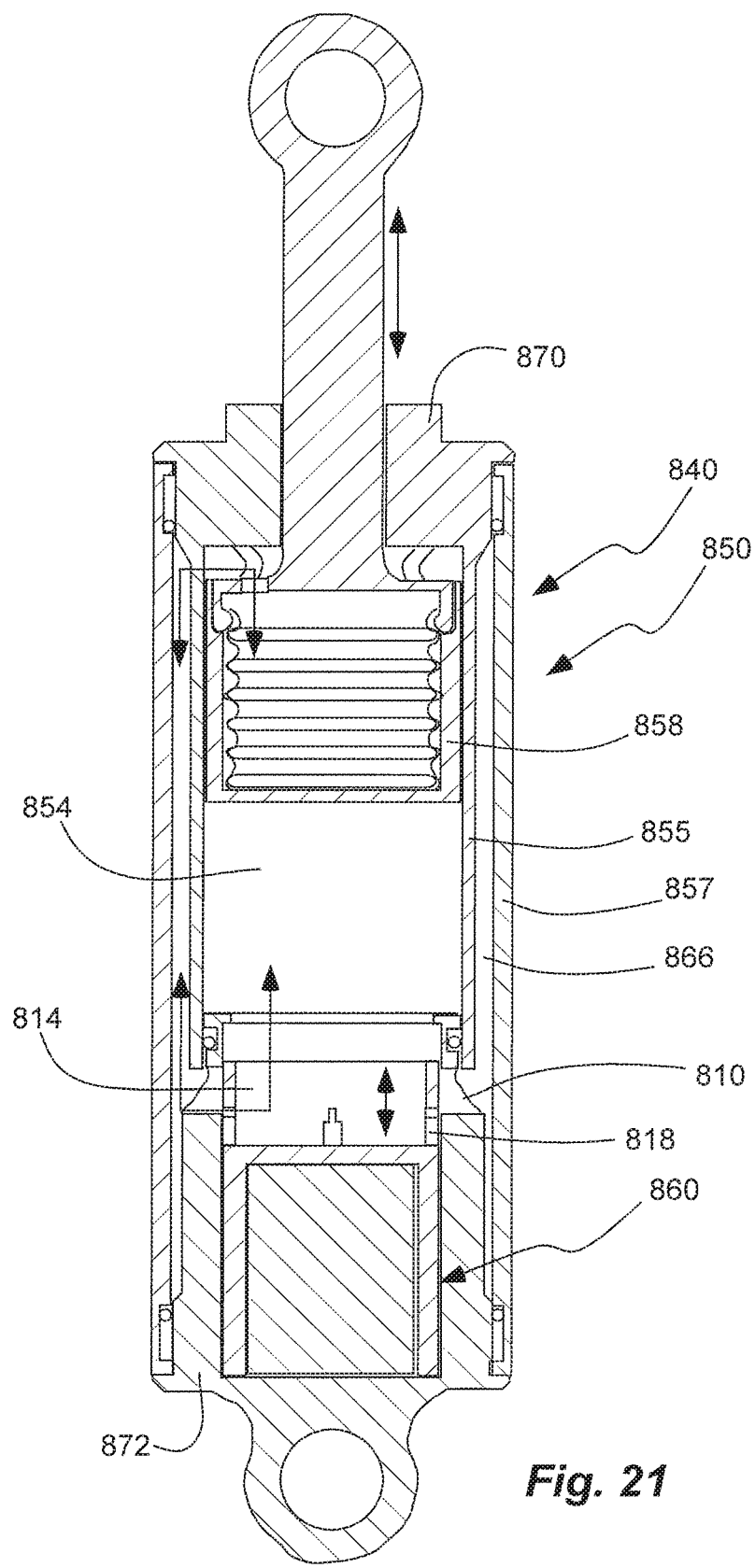
FIG. 21 is a cross-sectional side view of another hydraulic system of the prosthetic knee in accordance with another embodiment of the present invention employing the use of a twin wall cylinder, which arranges the fluid flow in dual concentric tubes, with one embodiment consisting of an inner working chamber (inner wall) containing a piston, and an outer concentric chamber (outer wall) providing the flow return circuit from one side of the piston to the other.

Referring to FIG. 21, another hydraulic system 840 for a prosthetic knee is shown in accordance with an embodiment of the present invention, which is similar in most respects to those described above, and which description is hereby incorporated herein by reference, but with a twin wall cylinder piston type hydraulic actuator or damper 850 to provide a compact cylindrical dimension. The actuator or damper 850 can include a double walled cylinder 854 with a piston 858 disposed in an inner cylinder or tube 855. An outer cylinder or tube 857 can circumscribe the inner cylinder 855 and form a hydraulic flow channel 866 therebetween. Thus, the cylinders 855 and 857 and the flow channel 866 can be concentric. The inner and outer cylinders can define a pair of concentric cylinders.

The outer cylinder or tube 857 can be disposed between opposite caps 870 and 872. One cap 870 can be formed integrally with the inner cylinder or tube 855 with the inner cylinder or tube 855 extending from the cap 870 into the outer cylinder or tube 857. An opposite cap 872 can close both the opposite ends of the inner and outer cylinders 855 and 857 opposite the first cap. The control valve or voice coil valve 860 can be carried by and disposed in the opposite cap 872. Thus, both the piston and the control valve are disposed in the outer cylinder 857, while the piston is disposed in the inner cylinder 855. The control valve or voice coil valve can be aligned with, parallel with, and/or have concentric axis with the piston.

An orifice 810 can be formed in the cap 872 and the control valve or voice coil valve 860 can include a spool 814 movable with respect to the cap 872 and the orifice 810. The spool 814 can have an opening 818 selectively movable and alignable with the orifice 810, as described above. The control valve actuation and the piston damper share a common centerline.

The piston 858 can include a reservoir therein to form a fluid compensator. The hydraulic fluid moves from one side of the piston to the other by flowing around the circumference of the area traveled by the piston.

Figure 22:
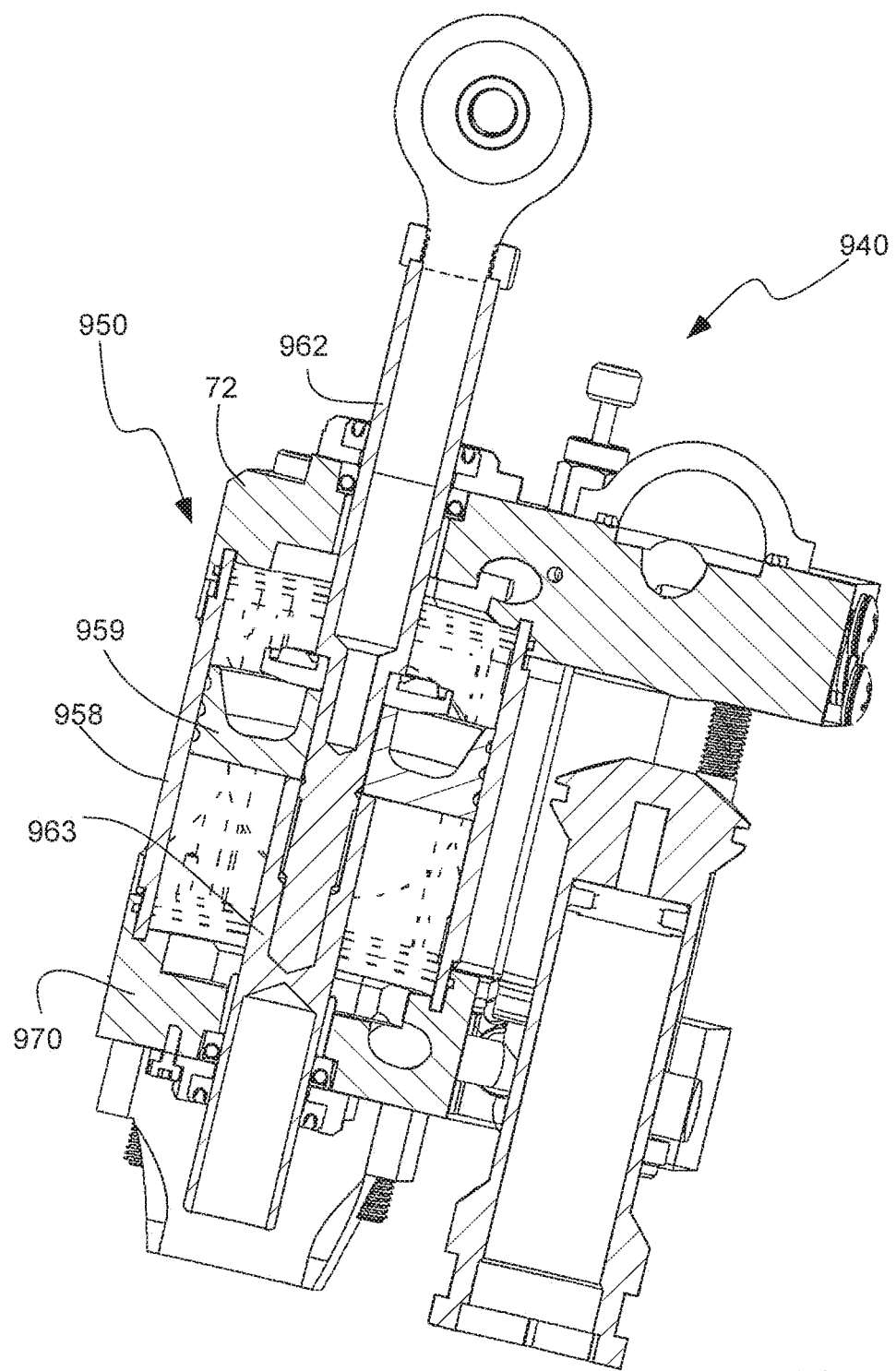
FIG. 22 is a cross-sectional side view of another hydraulic system in accordance with another embodiment of the present invention employing a through rod cylinder (shown with the control valve or voice coil valve separate from a housing thereof)
Figure 23:
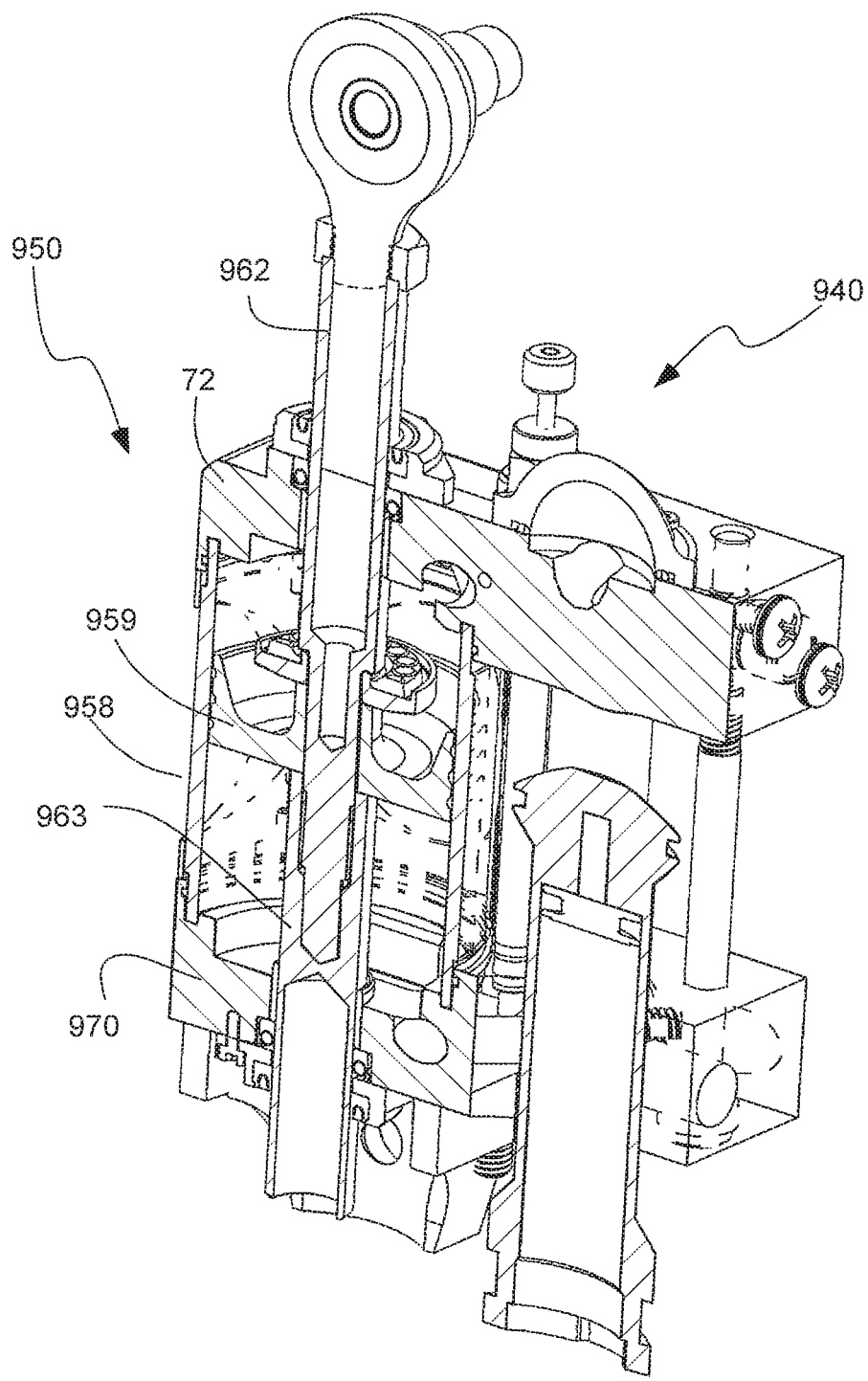
FIG. 23 is a cross-sectional perspective view of the hydraulic system of FIG. 22 (shown with the control valve or voice coil valve separate from a housing thereof).

As described above, an opposite rod can be formed on the piston on the opposite side of the piston rod so that the opposite chambers change volume equally. Referring to FIGS. 22 and 23, another hydraulic system 940 for a prosthetic knee is shown in accordance with an embodiment of the present invention, which is similar in most respects to those described above, and which description is hereby incorporated herein by reference, but with a through rod piston cylinder type hydraulic actuator or damper 950 which will not require a variable volume to operate as equal amounts of shaft or rod enter and leave the cylinder at the same time.

The hydraulic actuator or damper 950 includes a hydraulic chamber, namely a hydraulic cylinder 954, pivotally coupled to the lower member, and a piston 958 with a piston rod 962 pivotally coupled to the upper member. The piston 958 divides the chamber or cylinder 954 into opposite sides. The cylinder 954 can be formed by a cylinder disposed between opposite caps 970 and 72, one of which can be a lower cap 970 that can be pivotally coupled to the lower member, and the other of which can be an upper cap 72 that has an aperture to slidably receive the piston rod 962 that can be pivotally coupled to the upper member. The piston rod extends from the piston and out one side of the cylinder or chamber. In addition, the hydraulic actuator or damper 950 and/or piston 958 includes an opposite or through rod 963 extending from an opposite side of the piston from the piston rod 962. The opposite rod extends out an opposite side of the cylinder or chamber. The lower cap 970 has an aperture to slidably receive the opposite rod 963. The opposite rod 963 can have the same diameter, and thus the same volume, as the piston rod 962. Thus, as the piston 958 slides or displaces through the cylinder 954, the same amount of hydraulic fluid is displaced in both directions, reducing or eliminating the need for an overflow reservoir. Thus, the chamber or cylinder has a constant volume as the piston and rods move therein.

The piston rod 962 and the opposite rod 963 can be coupled together, such as by screwing a male threaded end of one into a female threaded bore in the end of the other. The piston 958 can be sandwiched or clamped between the two rods. Thus, one or both rods can pass through an aperture in the piston. An annular channel (radially facing) can be formed in one of the rods and between the rods to receive the piston therein. In addition, an annular bumper and/or stop 959 can be carried by the rods (such as sandwiched therebetween along with the piston) adjacent the piston to abut to one of the caps (such as cap 72) at the end of the travel of the piston. The bumper and/or stop 959 can include an annular rigid tray with an annular channel (facing axially) to receive an annular bumper member formed of a flexible and resilient material, and/or an elastic material. Thus, the bumper and stop can provide a cushion or soft feel to extension of the hydraulic system and extension of the knee.

The through rod piston cylinder type hydraulic actuator or damper 950 without a variable volume has a cylinder or working chamber with a constant volume that can create the same forces in both directions and in both tension and compression, with no need to displace the variable volume before creating force on one side. If high force is needed on the side of the piston or cylinder or working chamber which would have encompasses the variable volume in a cylinder without the through rod, and if high spring rate is needed in the variable volume to balance the force of moving this variable volume out of the way, then potentially cavitating of the oil can occur because the metering orifice is closed and fluid is not flowing. With through rod piston cylinder type hydraulic actuator or damper 950, however, a high spring rate variable volume, which would increase energy consumption on an above knee amputee as he/she initiates swing flexion, is not needed, and lower total energy consumption is a net result.

In addition, the cylinder 954 can be pivotally coupled to the lower member (or upper member) by the cap 970. The opposite sides of the cap 970 can be pivotally coupled to the lower member on lateral sides of the cylinder, cap or opposite rod 963 with the opposite rod 963 extending and/or displacing through the pivot axis to form a compact hydraulic system, as shown in FIG. 23.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A prosthetic device, comprising:
   a) a pair of prosthetic members movably coupled together to allow movement of the pair of prosthetic members with respect to one another;
   b) a hydraulic actuator or damper including hydraulic fluid in a hydraulic chamber coupled to one of the pair of prosthetic members, and a hydraulic piston movably disposed in the hydraulic chamber and coupled to another of the pair of prosthetic members;
   c) a hydraulic flow channel fluidly coupled between opposite sides of the chamber to allow hydraulic fluid to move between the opposite sides of the chamber as the hydraulic piston moves therein; and
   d) a voice coil valve coupled to the hydraulic flow channel to vary resistance to flow of hydraulic fluid through the flow channel, wherein the voice coil valve in a non-powered state allows a hydraulic fluid to move between the opposite sides of the chamber through a separate hydraulic flow channel.

2. The device of claim 1, wherein the voice coil valve comprises a safety port.

3. The device of claim 2, wherein the voice coil valve comprises an orifice, a spool, and the safety port is through the spool.

4. The device of claim 3, wherein the safety port is aligned with the orifice in the non-powered state.

5. The device of claim 4, wherein the safety port is biased to be aligned with the orifice in the non-powered state.

6. The device of claim 1, wherein the voice coil valve is reciprocally positionable with current polarity induced, bi-directional movement, by selectively changing a polarity of an electric current applied to the voice coil valve, such that the voice coil valve is selectively positioned and bi-directionally driven in back and forth directions.

7. The device of claim 6, wherein the voice coil valve is selectively positionable proportional to an amount of the electric current applied to the voice coil valve, such that a selective and variable amount of electric current applied to the voice coil valve selectively and proportionally varies the resistance of the voice coil valve to the flow of hydraulic fluid through the flow channel.

8. The device of claim 1, wherein the voice coil valve includes a permanent magnet and a coil movable with respect to one another; and wherein an electric current applied to the coil causes a spool to move in either a first direction or a second direction based on a polarity of the electric current.

9. The device of claim 8, wherein a force generated by the coil is directly proportional to the electric current applied.

10. The device of claim 1, wherein the voice coil valve has a substantially linear time and force response.

11. The device of claim 1, wherein the hydraulic flow channel comprises an orifice and a spool movable with respect to one another to selectively resist flow of the hydraulic fluid through the orifice.

12. The device of claim 11, wherein the voice coil valve comprises an electric actuator coupled to the hydraulic valve to move the orifice and the spool with respect to one another, including a permanent magnet and a coil movable with respect to one another, and reciprocally positionable with current polarity induced, bi-directional movement, by selectively changing the polarity of the electric current applied to the electric actuator, such that the spool is selectively positioned and bi-directionally driven in back and forth directions, such that the hydraulic valve varies resistance to the flow of hydraulic fluid through the flow channel.

13. The device of claim 1, wherein the voice coil valve has a coil and a spool with a path of travel parallel with a path of travel of the piston.

14. The device of claim 1, wherein the voice coil valve is disposed in and carried by the piston, and movable with the piston inside the hydraulic chamber, and the hydraulic channel extends through the piston.

* * * * *